United States Patent
Vitari et al.

(10) Patent No.: US 10,709,391 B1
(45) Date of Patent: Jul. 14, 2020

(54) METHOD OF CELL TAGGING FOR CANCER DETECTION

(71) Applicant: Verily Life Sciences LLC, Mountain View, CA (US)

(72) Inventors: Alberto Clemente Vitari, San Francisco, CA (US); Andrew Homyk, Belmont, CA (US); Joshua Simon Klein, Mountain View, CA (US); Marija Pavlovic, Mountain View, CA (US); Jerrod Joseph Schwartz, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 1191 days.

(21) Appl. No.: 14/956,608

(22) Filed: Dec. 2, 2015

(51) Int. Cl.
*A61B 5/00* (2006.01)
*A61B 5/1455* (2006.01)
*A61B 6/00* (2006.01)
*A61B 5/055* (2006.01)

(52) U.S. Cl.
CPC ............ *A61B 5/7271* (2013.01); *A61B 5/055* (2013.01); *A61B 5/1455* (2013.01); *A61B 5/6801* (2013.01); *A61B 6/481* (2013.01); *A61B 2562/0223* (2013.01)

(58) Field of Classification Search
CPC ..... A61B 5/7271; A61B 5/055; A61B 5/1455; A61B 5/6801; A61B 6/481; A61B 2562/0223
See application file for complete search history.

(56) References Cited

U.S. PATENT DOCUMENTS

| | | | |
|---|---|---|---|
| 2007/0098638 A1* | 5/2007 | Achilefu | A61B 5/0059 424/9.6 |
| 2009/0093728 A1* | 4/2009 | Hyde | A61B 1/041 600/476 |
| 2011/0104069 A1* | 5/2011 | Xu | A61K 9/0048 424/9.6 |
| 2015/0126861 A1* | 5/2015 | Gambhir | A61B 8/4427 600/431 |
| 2016/0252532 A1* | 9/2016 | Schilling | A61B 5/055 424/9.3 |

OTHER PUBLICATIONS

Sakabe, U.Y., et al., "Rapid Response Activatable Molecular Probes for Intraoperative Optical Image-Guided Tumor Resection," Hepatology, vol. 56, No. 3, p. 1170-1173 (2012).

(Continued)

*Primary Examiner* — Peter Luong
(74) *Attorney, Agent, or Firm* — McDonnell Boehnen Hulbert & Berghoff LLP

(57) ABSTRACT

Body-mountable devices are provided to detect the presence or status of a tumor in a body by detecting probes associated with circulating cells of the tumor that travel to subsurface vasculature of the body. The probe enters a tumor and associates with cells of the tumor before the cells metastasize. A wearable body-mountable device can be worn for a protracted period of time to detect the probe associated with circulating tumor cells in the vasculature at low concentrations and/or at low rates. A body-mounted device could detect the presence of such released, tumor-cell-associated probes to determine a presence or status of a tumor in the body.

20 Claims, 8 Drawing Sheets

(56) References Cited

OTHER PUBLICATIONS

Warren, A.D., et al., "Point-of-care diagnostics for noncommunicable diseases using synthetic urinary biomarkers and paper microfluidics," PNAS, Vo. 111, No. 10, p. 3671-3676 (2014).
Warren, A.D., et al., "Disease Detection by Ultrasensitive Quantification of Microdosed Synthetic Urinary Biomarkers," Journal of the American Chemical Society, vol. 136, p. 13709-13714 (2014).
Goergen, C.J., et al., "In vivo fluorescence lifetime detection of an activatable probe in infarcted myocardium," Journal of Biomedical Optics, vol. 17(5), p. 056001-1-6, (2012).
Weissleder, R., et al., "In vivo imaging of tumors with protease-activated near infrared fluorescent probes," Nature Biotechnology, vol. 17, p. 375-378 (1999).
Tannock, I.F., et al., "Acid pH in Tumors and Its Potential for Therapeutic Exploitation," Cancer Research, vol. 49, p. 4373-4384, (1989).
Mallidi, Srivalleesha, et al., "Photoacoustic imaging in cancer detection, diagnosis, and treatment guidance," Trends Biotechnol., vol. 29(5), p. 213-221 (2011).
Condeelis, J., et al., "In Vivo Imaging in Cancer," Cold Spring Harb Perspect. Biol., vol. 2, p. 1-22 (2010).
Mehrmohammadi, M., et al., "Photoacoustic Imaging for Cancer Detection and Staging," Curr Mol Imaging, vol. 2 (1), p. 89-105 (2013).
Faltas, B., "Cornering metastases: therapeutic targeting of circulating tumor cells and stem cells," Frontiers in Oncology, vol. 2, Article 68, p. 1-7 (2012).
Stuker, F., "Fluorescence Molecular Tomography: Principles and Potential for Pharmaceutical Research," Pharmaceutics, vol. 3, p. 229-274 (2011).
Galanzha, E.I., "Circulating Tumor Cell Detection and Caputre by Photoacoustic Flow Cytometry in Vivo and ex Vivo," Cancers, vol. 5, p. 1691-1738 (2013).
Nima, Z.A., et al., "Circulating tumor cell identification by functionalized silver-gold nanorods with multicolor, super-enhanced SERS and photothermal resonances," Scientific Reports, vol. 4, 4752, p. 1-8 (2014).
Galanzha, E.I., et al., "In vivo magnetic enrichment and multiplex photoacoustic detection of circulating tumour cells," Nat. Nanotechnol., vol. 4 (12), p. 855-860 (2009).
Lin, K.Y., et al., Nanoparticles that Sense Thrombin Activity as Synthetic Urinary Biomarkers of Thrombosis, ACS Nano, vol. 7(10). p. 9001-9009 (2013).
Kwong, G.A., "Mass-encoded synthetic biomarkers for multiplexed urinary monitoring of disease," Nature Biotechnology, vol. 31, No. 1, p. 63-71 (2013).
Danino, T., et al., "Programmable probiotics for detection of cancer in urine," Science Translational Medicine, vol. 7, Issue 289, p. 1-12 (2015).

\* cited by examiner

US 10,709,391 B1

METHOD OF CELL TAGGING FOR CANCER DETECTION

BACKGROUND

Unless otherwise indicated herein, the materials described in this section are not prior art to the claims in this application and are not admitted to be prior art by inclusion in this section.

A number of scientific methods have been developed to detect, measure, and/or affect one or more analytes in a biological or other environment (e.g., a person's body). The one or more analytes could be any analytes that, when present in or absent from a person's body, or present at a particular concentration or range of concentrations, may be indicative of a medical condition or health state of the person. The one or more analytes could be substances whose distribution, action, or other properties, interactions, or activities throughout an animal's body is of scientific or medical interest. The one or more analytes could include pharmaceuticals or other substances introduced into the biological or other environment to effect some chemical or biological process, or to be affected by such a chemical or biological process. The one or more analytes could be present in living or nonliving human or animal tissue, and could be detected, measured, or affected in an in vivo, ex vivo, in vitro, or some other type of sample. The one or more analytes could include probes introduced into a body in order to provide contrast or to otherwise enable the detection of an analyte or physical variable in the body.

SUMMARY

Some embodiments of the present disclosure provide a body-mountable device that includes: (i) a sensor that is configured to be mounted to an external body surface of a body proximate a portion of subsurface vasculature and that is configured to detect a probe in the portion of subsurface vasculature; (ii) a controller that is operably coupled to the sensor and that includes a computing device programmed to perform controller operations. The probe is configured to associate with tumor cells before the tumor cells metastasize and to remain associated with the tumor cells after the tumor cells have metastasized. The controller operations include: (1) operating the sensor to detect the probe, wherein detecting the probe includes measuring an amount of the probe in the portion of subsurface vasculature; and (2) determining a tumor presence or status based on the measured amount of the probe in the portion of subsurface vasculature.

Some embodiments of the present disclosure provide a method that includes operating a body-mountable device that includes a sensor that is mounted to an external body surface of a body proximate to a portion of subsurface vasculature. The sensor of the body-mountable device is configured to detect a probe in the portion of the subsurface vasculature. The probe is configured to associate with tumor cells before the tumor cells metastasize and to remain associated with the tumor cells after the tumor cells have metastasized. Operating the body-mountable device includes: (i) detecting, using the sensor of the body-mountable device, the probe in the portion of subsurface vasculature, wherein detecting the probe includes measuring an amount of the probe in the portion of subsurface vasculature; and (ii) determining a tumor presence or status based on the measured amount of the probe in the portion of subsurface vasculature.

These as well as other aspects, advantages, and alternatives, will become apparent to those of ordinary skill in the art by reading the following detailed description, with reference where appropriate to the accompanying drawings.

DETAILED DESCRIPTION

Figure 1:
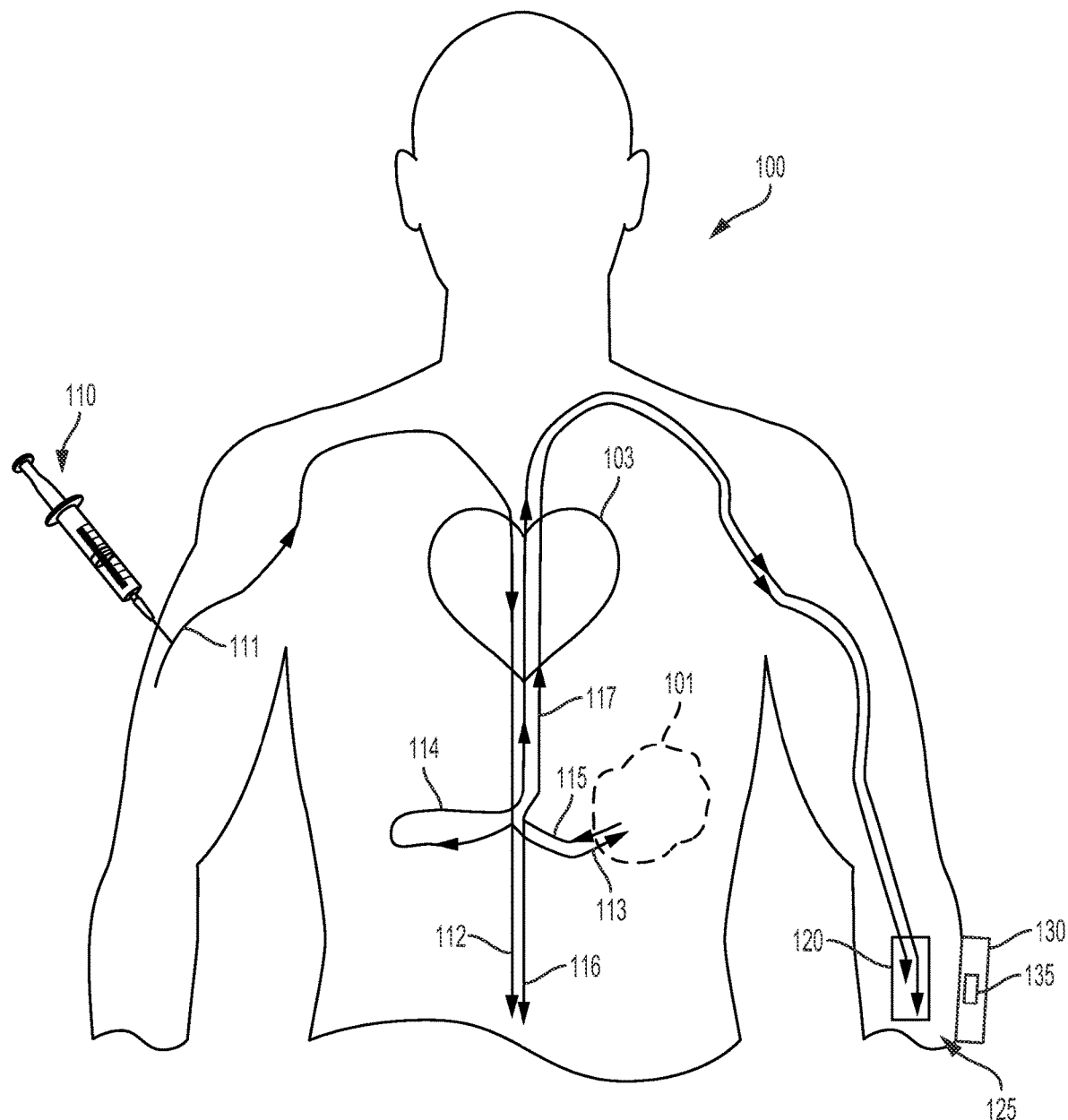
FIG. 1 is a schematic diagram of a human body, showing movement within the body of a probe that has been introduced into the body, in accordance with an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

It can be beneficial to detect the presence, status, location, or other properties of cancerous tumors in a human body. A course of treatment (e.g., a chemotherapeutic regimen, a surgical intervention) can be determined based on a detected presence, location, status (e.g., size, stage of cancer, type of cancer, degree or rate of metastasis), or other detected properties of a tumor.

However, detection of such properties of a tumor can be difficult. This difficulty can be related to the location of a tumor within deep tissues of the body, making detection (e.g., through fluorescence imaging, X-ray imaging, magnetic resonance (MR) imaging, or other imaging modalities) difficult due in part to the presence of intervening tissues between the tissue and any devices used to image the tumor. Alternatively, properties of the tumor could be detected based on properties of circulating tumor cells (CTCs) emitted into the circulation by the tumor. However, such detection can be difficult due to the rarity of such CTCs in the blood.

In order to detect properties of a tumor, a probe that is configured to associate with cells of the tumor can be introduced into the body (e.g., via intravenous injection). The probe could associate with the tumor cells before the cells metastasize and could remain associated with the tumor cells after the tumor cells have metastasized. Such a probe could then travel, with the metastasized tumor cells via the circulatory system of the body, to a location near an external surface of the body (e.g., to a portion of subsurface vasculature). Once proximate to the surface of the body, the probe could be detected by a body-mountable device. The body-mountable device could operate to detect the probe and such detection could be used to determine a presence or status of the tumor. This could include mounting the body-mountable device to an external body surface (e.g., a skin surface) such that a sensor of the body-mountable device is located proximate a portion of subsurface vasculature beneath the external body surface. The sensor could then detect the presence or other properties of the probe in the portion of subsurface vasculature. Such a body-mountable device could include a hand-held or desktop device that could be mounted to a skin surface by placing the device in contact with the skin surface and/or by moving an arm or other body part to contact the device. Additionally or alternatively, the body-mountable device could be a wearable device (e.g., a wrist-mountable wearable device) that could be worn on a body surface. Such a wearable body-mountable device could operate, over a protracted period of time, to detect potentially infrequent release of tumor cells from the tumor.

Such a probe could be configured to associate with tumor cells in a variety of ways. For instance, the probe could be configured to bind to the outside of the tumor cells. Additionally or alternatively, the probe could be deposited within a tumor cell (e.g., by inducing endocytosis of the probe by the tumor cell). The probe could be configured to associate with the tumor cells in response to the presence of tumor-cell-specific membrane proteins on the tumor cells or other properties of the tumor cells themselves. Additionally or alternatively, the probe could be configured to associate with the tumor cells in response to exposure to factors of the environment within the tumor. For example, a pH, an oxygen content, an amount of lactic acid, the presence of a tumor-specific protease, or some other aspect of the environment within the tumor could cause association of a probe present in the tumor with cells of the tumor.

Further, such a probe could have a property that is related to exposure of the probe to a tumor. For example, the probe could have a fluorescence intensity that increases or decreases as a result of exposure to the tumor. In such examples, the detection of such a property of the probe (e.g., in a portion of subsurface vasculature by a body-mountable device mounted proximate thereto) could be used to determine the presence or status of the tumor.

Extended periods of time (e.g., days, weeks, months) can elapse between the association of a probe with tumor cells and the metastasis of the tumor cells (as CTCs) into the circulation. As such, the probe can be configured to have a detectable element (e.g., a magnetic element, a fluorescent element) that is stable within the body over such extended time periods (that is, that can still be detected in a portion of subsurface vasculature, by a body-mountable device, after having been located within the body for the extended period of time). For instance, the probe could include a magnetic nanoparticle (e.g., a particle of superparamagnetic iron), a fluorescent nanodiamond (e.g., a particle of nanodiamond that includes one or more fluorescent defects), a fluorescent quantum dot (e.g., a quantum dot composed of stacked layers of semiconductor materials), or some other element that is not substantially degraded by the human body. Additionally or alternatively, a detectable element of the probe could be disposed within a layer of protective material (e.g., a protective coating of polystyrene). Other methods are anticipated for preserving a detectable element of the probe while disposed within the human body for extended periods of time.

The probe could have a variety of properties that could be detected by a body-mountable device when the probe is located within a portion of subsurface vasculature. Such properties could be used to detect the presence of the probe and/or such properties could be related to the exposure of the probe to a tumor environment. In some examples, the probe could include a fluorophore, a Raman dye, or some other optically active material having a fluorescence intensity, an excitation spectrum, an emission spectrum, an absorption spectrum, a color, or some other optical property that could be detected. Additionally or alternatively, the probe could include magnetic material (e.g., a magnetic chemical moiety, a nanoparticle of superparamagnetic iron) and a coercivity, a susceptibility, an intrinsic or induced magnetic field, a hysteresis curve, a magnetic resonance, or some other magnetic property of the probe could be detected. The probe could include multiple such detectable elements.

The presence or status of a tumor can be detected, based on detected properties of the probe in a portion of subsurface vasculature, in a variety of ways. If the probe is absorbed into the tumor or other tissues and is released substantially only from the tumor (e.g., due to the probe being associated with tumor cells and being released with the tumor cells when they metastasize, or the probe being released from an aggregate or other anchor as a result of exposure to the tumor environment), detection of the probe in the portion of subsurface vasculature can indicate the presence of the tumor, a size of the tumor, a type of the tumor, a rate of metastasis or the tumor, or some other status information about the tumor. If the probe has a property that is related to exposure to the tumor (e.g., a fluorescence intensity that is increased by exposure to the tumor), the presence, size, type, or some other status information about the tumor can be determined based on the detected property.

Those of skill in the art will understand a "probe" in its broadest sense and that it may take the form of any fabricated material, a molecule, cryptophane, a virus, a phage, etc. or some combination thereof. In practice, a plurality of probes will be administered to a body, and one or more of the administered probes can then be detected, in a portion of subsurface vasculature, by a body-mountable device mounted proximate the portion of subsurface vasculature or by some other device disposed on or within the body. The probe can include one or more detectable elements, e.g., fluorophores, Raman dyes, dyes, magnetic nanoparticles, quantum dots, fluorescent nanodiamonds, or other elements that can be detected by magnetic, optical, or other methods. The probe can be configured to selectively bind to one or more analytes (e.g., chemicals, hormones, peptides, DNA or RNA fragments, cells), for instance, to bind to tumor cells and/or to be incorporated within such cells. The probe could include one or more elements configured to be cleaved, to be denatured, to change a conformation, or to be otherwise modified by exposure to one or more conditions in the environment of a tumor, e.g., to a pH level, a concentration of lactic acid, an oxygen level, a concentration of one or more cancer-type-specific proteases, or some other conditions present in a tumor.

It should be understood that the above embodiments, and other embodiments described herein, are provided for explanatory purposes, and are not intended to be limiting.

Further, the term "tumor" as used herein should be understood broadly to include any mass of abnormal tissue growth within a body, e.g., a neoplasm. A tumor as described herein could be a benign tumor or a malignant tumor. A tumor could be a primary tumor (e.g., a mass of cells at the anatomical site of an original tumor cell) or a secondary tumor (e.g., a mass of cells grown from one or more cells that metastasized from an original tumor. A tumor could be formed from brain cancer cells, breast cancer cells, skin cancer cells, colon cancer cells, esophageal cancer cells, pancreatic cancer cells, or some other type of cancer cells. Accordingly, the environment within a tumor could have a pH, a distribution of proteases, proteins, or other analytes, a temperature, an oxygen content, or some other properties that are related to the type of cells present in the tumor and/or on the structure of the tumor.

II. DOWNSTREAM DETECTION OF TUMOR PROPERTIES USING EXOGENOUS PROBES

As noted above, it can be difficult to detect the presence, status, or other information about a tumor located within a body. Imaging contrast agents (e.g., X-ray contrast agents, MR contrast agents) can be used to image a tumor, but such imaging may involve the use of large, expensive imaging equipment (e.g., CT scanners, MR imagers), limiting the frequency and convenience of such options. Conversely, exosomes, circulating tumor cells (CTCs), or other analytes emitted from the tumor could be detected in the bloodstream (e.g., in a sample of blood drawn from the body), but such analytes can be rare and difficult to specifically detect.

As an alternative, a probe that is configured to travel through the circulation to a tumor could be introduced into the body (e.g., by intravenous injection). The probe could then interact with the tumor in some way, and subsequently leave the tumor to re-enter the circulation. Such probes could then be detected when they travel through the peripheral circulation (e.g., through a portion of subsurface vasculature that is easily visible through the skin by a body-mountable device) and the presence or status of the tumor could be determined based on the detection of the probes and/or the detection of one or more properties of the probes.

As an illustrative example, FIG. 1 shows the motion of a probe through a human body 100. The body 100 includes a tumor 101. The probe is injected into the bloodstream of the body 100 by a syringe. The heart 103 of the body 100 pumps blood through the vasculature of the body; as a result, the injected probe travels 111 from the site of the injection to the heart 103. The probe can then travel to a variety of locations in the body, and may circulate multiple times through the heart 103 before exiting the circulation and/or being destroyed or disabled.

In a first example path 114, the probe circulates through the vasculature without interacting with the tumor 101 and eventually passes through a portion of subsurface vasculature 120 proximate to which a body-mountable device 130 is mounted. A sensor 135 of the body-mountable device 130 could detect the probe, e.g., could detect the presence of the probe in the portion of subsurface vasculature 120 and/or could detect some property of the probe (e.g., a fluorescence intensity) that is related to whether the probe has been exposed to the tumor 101. In a second example path 112, some of the probes that have not interacted with the tumor 101 are removed from the circulation. This could include being falling out of the circulation into non-tumor tissues, being damaged or destroyed by the environment of the body, being eliminated as waste (e.g., by the kidneys or liver), or being otherwise eliminated or deactivated. A third example path 113 shows some of the introduced probes leaving the circulation and entering the tumor 101.

The introduced probes could preferentially enter the tumor 101 (rather than being recirculated through the vasculature, being deposited in other tissues, or being eliminated via the kidneys) due, in part, to the enhanced permeability and retention (EPR) effect of the tumor 101. The EPR effect is a property of many tumor types by which certain contents of the blood (e.g., liposomes, nanoparticles, macromolecular drugs) accumulate within a tumor. This effect can be related to the vasculature within the tumor being fenestrated (e.g., having more holes than vasculature in other tissue) or otherwise formed differently from vasculature in other tissues (e.g., by lacking a smooth muscle layer or by exhibiting some other modified properties). The EPR effect can additionally or alternatively be related to a decreased amount of lymphatic drainage from tumor tissues relative to other tissues. The probe and/or an aggregate or other substance that includes the probe could have a size, geometry, or other properties specified based on properties of the EPR effect to increase the likelihood of the probe leaving the vasculature to enter the tumor 101.

Such probes that enter the tumor 101 could then exit the tumor (shown as example path 115). In some examples, probes could exit the tumor as a result of being released from an aggregate or other anchoring substance. Additionally or alternatively, a probe could be associated with (e.g., bound to, disposed within) a tumor cell and the probe could exit the tumor 101 as a result of the tumor cell metastasizing from the tumor 101. As illustrated by example path 116, some of the probes that have interacted with and exited the tumor 101 will leave the bloodstream (e.g., via the kidneys or liver, or by deposition in tissues of the body) and/or be damaged or destroyed by the body (e.g., by the action of the immune system of the body and/or by exposure to the pH or other factors of the blood). Alternatively, some of the probes that exit the tumor 101 could travel (as shown by example path 117) to the portion of subsurface vasculature 120 to be detected by the sensor 135 of the body-mountable device 130. The presence or status (e.g., type, size, stage, rate or degree of metastasis) of the tumor 101 could then be determined based on the detection of such probes.

As illustrated in FIG. 1, the probe is introduced into the body 100 using a hypodermic syringe 110. However, the probe could be introduced into the bloodstream in a variety of other ways. For example, the probe could be introduced via a catheter, intravenous port, a transdermal patch or other transdermal delivery means, or other means for accessing the vasculature. Additionally or alternatively, the probe could be administered orally (e.g., in a pill or other ingestible substance) and could be absorbed by the body into the bloodstream.

As illustrated in FIG. 1, the body-mountable device 130 is mounted to a wrist of the body 100 in order to detect probes that may be present in the portion of subsurface vasculature 120 located beneath skin of the wrist. The body-mountable device 130 could be configured to be mounted to a skin surface proximate some other portion of subsurface vasculature, e.g., an ankle, an arm a leg, a location on the torso, or some other location where probes in subsurface vasculature can be detected, e.g., by detecting a magnetic field, an electromagnetic field, a light, or some other energy or field produced by the probe. Further, as noted above, some of the probes detected in such a portion of subsurface vasculature by such a body-mountable device could include probes that have not been released from, passed through, been modified by, or otherwise interacted with a tumor (e.g., 101).

The sensor 135 could detect a variety of physical variables in order to detect a probe in the portion of subsurface vasculature 120. In some examples, the sensor 135 could be configured to detect an intensity, a spectrum, a color, or some other property of light reflected, refracted, fluorescently absorbed and re-emitted, scattered, or otherwise emitted by the probe (e.g., by a fluorophore, chromophore, Raman dye, fluorescent nanodiamond, or other element of the probe). Additionally or alternatively, the sensor 135 could directly or indirectly detect a magnetic field produced by the probe (e.g., by a nanoparticle of superparamagnetic iron or other magnetic element of the probe). The sensor 135 could detect some other physical variable that is related to the presence of the probe in the portion of subsurface vasculature 120 proximate the sensor 135 and/or that is related to a property of the probe that is indicative of whether the probe has interacted with the tumor 101. Based on such detected physical variables, the presence, number, location, or other properties of probes in the portion of subsurface vasculature 120 could be determined. Further, in some examples, such detected physical variables could be used to determine whether a particular probe has interacted with a tumor, to determine how long the probe interacted with the tumor, to determine a property of the tumor (e.g., a pH level in the tumor, a tumor type), or to determine some other information.

The presence or status of the tumor 101 could be determined based on the detection of the probe and/or the detection of one or more properties of the probe. For example, the presence, size, type, rate of metastasis, stage, or other status information of the tumor 101 could be determined based on a rate at which the probe is detected in the portion of subsurface vasculature 120, a number of individual probes detected, or some other information about the rate or amount of the probe that is detected using the sensor 135. Additionally or alternatively, in examples wherein the probe has a property that is indicative of whether the probe has interacted with the tumor, such information about the tumor 101 could be determined based on the detected property of the probe. Such determinations could also be based on information about the introduction of the probe into the body 100, e.g., based on a timing or rate of introduction of the probe into the body 100 or based on an amount of the probe that is introduced into the body 100.

As noted above, there could be a protracted period of time (e.g., hours, weeks, months) between introduction of a probe into the body 100, absorption of the probes into the tumor 101 and/or interaction between the probe and the tumor 101, and release of the probes from the tumor 101 into the circulation such that the probe can travel to the portion of subsurface vasculature 120. The probe could be configured to be detectable (e.g., to have fluorophores, magnetic elements, or other detectable elements) over such extended periods of exposure to conditions within the body.

For example, the probe could include elements that are intrinsically stable within the body, e.g., resistant to chemical reaction, immune attack, dissolution, photobleaching, or other damaging processes within the body. Such intrinsically stable elements could include fluorescent nanodiamonds, particles of superparamagnetic iron or other magnetic materials, or quantum dots or rods or other fluorescent and/or plasmonic materials formed from semiconductors or from other materials that are substantially stable over extended periods of time when exposed to environments within the human body. Such stability could be related to exposure to the tumor environment, such that the detectable element is more stable within the tumor environment (where it may remain for a protracted period of time) and less stable when out of the tumor environment (e.g., within the portion of subsurface vasculature 120). For instance, the detectable element could be a pH-sensitive fluorophore and exposure of the fluorophore to the environment within the tumor (e.g., to a pH level characteristic of the tumor environment) could reduce a rate of photobleaching of the fluorophore (e.g., by changing an excitation or emission spectrum of the fluorophore and/or by quenching the fluorophore).

Additionally or alternatively, the probe could include protective structures to protect elements of the probe from damaging processes within the human body. For example, a fluorophore, magnetic nanoparticle, or other detectable element or material could be coated with or otherwise enclosed within a protective material, e.g., within a nanoparticle of polystyrene. In other examples, fluorophores or other detectable elements could be enclosed within liposomes or micelles for protection.

In examples in which the probe remains in the tumor 101 for a protracted period of time, the probe could be introduced into the body 100 in small amounts over an extended period of time. Introduction of a probe in small amounts could reduce undesirable effects on the kidneys, liver, or other body systems when compared to introduction of the probe in larger amounts. In one approach, the probe is configured to tag tumor cells before the cells enter the circulation, so as to allow subsequent detection of the tumor cells in circulation (as CTCs) by the body-mountable device 130 detecting the probe in the portion of subsurface vasculature 120. Smaller amounts of the probe can be administered to detect such CTCs than if the probe is configured to associate with the tumor cells after the cells have entered circulation. This lowered amount could be related to the rarity of such CTCs in the circulation at any particular point in time and/or to the low concentration of such CTCs in the circulation.

As noted above, probes as described herein could travel through the vasculature of a body to a tumor, interact with the tumor, and be detected downstream in a portion of subsurface vasculature by a body-mountable device. Based on the detected probe, a presence or status (e.g., size of the tumor, degree or rate of metastasis of the tumor, type of the tumor) of the tumor could then be determined. In some examples, the probe is configured to bind specifically to cells of the tumor, to re-enter the circulation from the tumor and not from other tissues, or to otherwise be present in the circulation in an amount that is related to the presence or status of the tumor; in such examples, detection of the probe in a portion of subsurface vasculature could be used to infer the presence or status of the tumor. Additionally or alternatively, the probe could have a property (e.g., a fluorescence intensity) that changes in response to interaction between the probe and the tumor (e.g., in response to exposure of the probe to the tumor environment); in such examples, such a detected property indicative of whether the probe has interacted with the tumor could be used to infer the presence or status of the tumor.

Figure 2A:
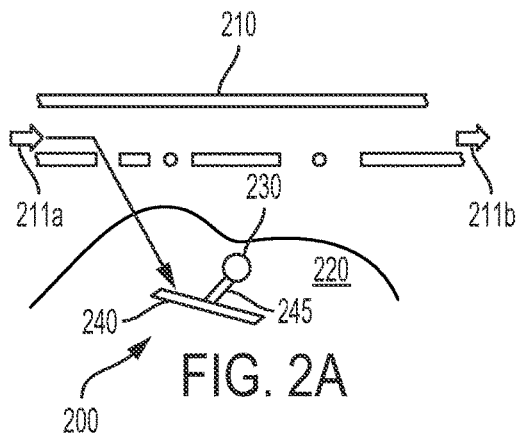
FIG. 2A is an illustration of a probe leaving a portion of vasculature and entering a tumor, in accordance with an example embodiment.

In some examples, a probe could be absorbed into tissues along with an aggregate (e.g., an aggregate of multiple instances of the probe) or other anchoring substance. If the probe (and associated aggregate or other anchoring substance) is absorbed into a tumor, the probe could be responsively released from the tumor into the bloodstream. Such a released probe could be detected downstream (e.g., in a portion of subsurface vasculature by a body-mountable device mounted proximate thereto) and used to determine the presence or status of the tumor. As an illustrative example, FIG. 2A shows a tumor 220 within a body and a portion of vasculature 210 proximate the tumor 220. Blood flows into 221a and out of 211b the portion of vasculature 210. The portion of vasculature 210 is fenestrated (i.e., has breaks in its walls); as a result, cells, macromolecules, probes, or other contents of the blood flowing into 221a the portion of vasculature 210 can leave the portion of vasculature 210 and interact with the tumor 210. For instance, and as illustrated in FIG. 2A, a probe aggregate 200 that includes a probe 230 attached to an anchoring element 240 via a linking element 245 has left the portion of vasculature 210 and been absorbed by the tumor 220.

The probe aggregate 200, linking element 245, probe 230, and/or the anchoring element 240 could include a variety of compounds or structures. Further, while a single probe 230 is illustrated as being attached to the anchoring element 240, more than one probe could be attached to a single anchoring element and/or the anchoring element 240 could itself comprise a number of probes. The anchoring element 240 could comprise a variety of substances configured to be absorbed into a tumor from the bloodstream. For instance, the anchoring element 240 could be a nanoworm composed of a plurality of nanoparticles of iron oxide that are coated in polyethylene glycol, dextran, or some other coating material. The anchoring element 240 could include elements configured to selectively bind to tumor cells (e.g., an aptamer, an antibody, a tumor-targeting peptide) to improve the targeting of the probe aggregate 200 to the tumor 220.

The linking element 245 could bind a fluorophore, a magnetic nanoparticle, a quantum dot, or other elements of the probe 230 to the anchoring element 240 until the probe aggregate 200 is absorbed into a tumor (e.g., 220). After the probe aggregate 200 is absorbed into a tumor, the linking element 240 could release the probe 230 back into the circulation, such that the probe 230 may be detected in superficial vasculature by a body-mountable device. This is illustrated by way of example in FIG. 2B, wherein the linking element has released the probe 230 from the anchoring element 245. This release could include the linking element 245 being cleaved, lysed, or otherwise modified in response to one or more factors (e.g., a pH level, an oxygenation level, a concentration and/or presence of a tumor-specific protease) present in the tumor 220. Also illustrated in FIG. 2B are other probe aggregates and/or anchoring elements that have been absorbed into the tumor 220.

Figure 2B:
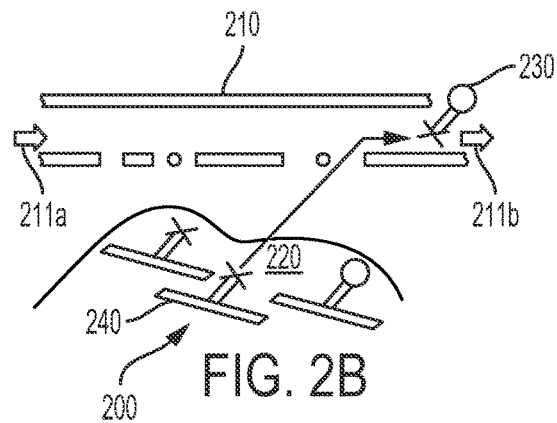
FIG. 2B is an illustration of the probe of FIG. 2A interacting with the tumor and leaving the tumor and entering the portion of vasculature, in accordance with an example embodiment.

As illustrated in FIGS. 2A and 2B, a probe that has been absorbed into a tumor can be released, from a probe aggregate that contains the probe and that has been absorbed into the tumor with the probe, in response to exposure of the probe and/or probe aggregate to tumor-specific properties of the tumor environment. As a result, detection of such released probes can provide information about the presence or status of the tumor. Additionally or alternatively, a probe could associate with cells of a tumor such that the probe remains associated with the tumor cells after the tumor cells metastasize from the tumor into the bloodstream.

Figure 3A:
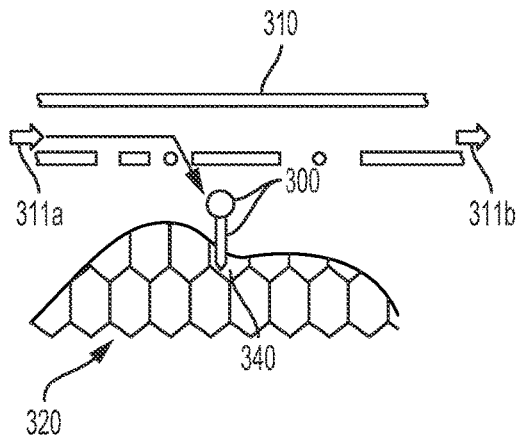
FIG. 3A is an illustration of a probe leaving a portion of vasculature and entering a tumor, in accordance with an example embodiment.

As an illustrative example, FIG. 3A shows a tumor 320 within a body and a portion of vasculature 310 proximate the tumor 320. The tumor 320 is comprised of a plurality of tumor cells, including a particular tumor cell 340. Blood flows into 321a and out of 311b the portion of vasculature 310. The portion of vasculature 310 is fenestrated (i.e., has breaks in its walls); as a result, cells, macromolecules, probes, or other contents of the blood flowing into 321a the portion of vasculature 310 can leave the portion of vasculature 310 and interact with the tumor 310. For instance, and as illustrated in FIG. 3A, a probe 300 has left the portion of vasculature 310 and associated with the particular tumor cell 340.

As illustrated in FIG. 3A, the probe 300 associating with the tumor cell 340 includes the cell binding to the outside of the tumor cell 340. Such binding could be facilitated by the probe 300 including elements configured to selectively bind to the outside of tumor cells (e.g., the probe 300 could include an aptamer, an antibody, a tumor-targeting peptide). Alternatively, the probe 300 could associate with a tumor cell by entering the tumor cell, e.g., by including recognition proteins or other elements configured to induce endocytosis of the probe 300 by a tumor cell. Further, the association of the probe 300 with a cell (e.g., a tumor cell) could be dependent upon one or more factors (e.g., a pH level, an oxygenation level, a concentration and/or presence of a tumor-specific protease) present in the tumor 320 in order to increase the specificity of association of the probe 300 with cells of the tumor 320. For example, an element of the probe that is configured to bind to or otherwise interact with tumor cells (e.g., an antibody, a receptor, an aptamer) could have a conformation that is dependent on pH such that the element only acts to bind to or otherwise interact with tumor cells when exposed to a pH that is typical of the environment within a tumor. In another example, an element of the probe could be configured to interfere with such a receptor or other binding agent of the probe (e.g., the probe could include a competitive agonist that is configured to bind to a receptor and that is tethered to the probe). Such an interfering element could be cleaved off or otherwise disabled due to exposure to a tumor environment (e.g., in response to a protease that is typically present in a tumor). In yet another example, the probe 300 could include a protective layer that is selectively degraded by exposure to the tumor environment (e.g., by a lowered pH characteristic of the tumor environment) and degradation and/or removal of the protective layer could allow for association of the probe 300 with tumor cells (e.g., could reveal an aptamer, antibody, receptor, or other element(s) of the probe 300 configured to cause selective association with tumor cells and/or to cause association with cells in general).

Figure 3B:
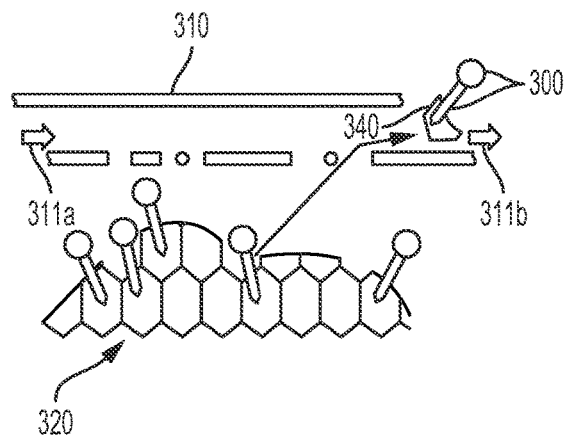
FIG. 3B is an illustration of the probe of FIG. 3A interacting with the tumor and leaving the tumor and entering the portion of vasculature, in accordance with an example embodiment.

The after the probe 300 is associated with a tumor cell (e.g., 340), the probe 300 could move back into the circulation when the associated tumor cell metastasizes into the circulation. The probe 300 may then be detected in superficial vasculature by a body-mountable device. This is illustrated by way of example in FIG. 3B, wherein the tumor cell 340 has metastasized into the portion of vasculature 310. As a result, detection of the released probe 300 can provide information about the presence or status of the tumor, e.g., a rate or stage of metastasis or progression of the tumor. Also illustrated in FIG. 3B are other probes that have associated with tumor cells in the tumor 320.

As noted above, a probe can additionally or alternatively have a property that is indicative of whether the probe has interacted with a tumor of the body. For example, a fluorescence intensity of the probe, an excitation spectrum of the probe, an emission spectrum of the probe, a size of the probe, a presence or absence of one or more elements of the probe, a magnetic moment of the probe, or some other property of a probe could be affected by interaction with a tumor. Such an interaction could include the probe being exposed to the environment within a tumor (e.g., to a pH level or an oxygen level characteristic of a tumor), the probe binding to tumor cells of the tumor, the probe catalyzing a reaction of a substance within the tumor and/or a substance within the tumor catalyzing a reaction of one or more elements of the probe (e.g., an element of the probe being cleaved, denatured, or otherwise altered by a protease that is characteristically present in the tumor), or some other interaction. Such interactions could effect a change in the indicator property of the probe by a variety of mechanisms. For example, an element (e.g., a fluorescence quencher, a fluorophore, a magnetic nanoparticle, a quantum dot) of the probe could be cleaved from the probe, denatured, damaged, dissolved, disabled, could experience a change in conformation or geometry, or otherwise altered as a result of interaction with the tumor. Additionally or alternatively, one or more elements could be added to the probe (e.g., a protein, an antibody, and antigen, a cell, a macromolecule) as a result of interaction with a tumor.

Figure 4A:
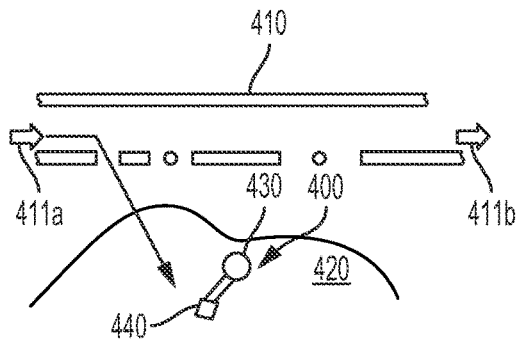
FIG. 4A is an illustration of a probe leaving a portion of vasculature and binding to a cell of a tumor, in accordance with an example embodiment.

A probe that has such a property indicative of whether the probe has interacted with a tumor of the body could interact with a probe that is located within a body, travel in the circulation to a portion of subsurface vasculature, and be detected by a body-mountable device proximate to the portion of subsurface vasculature. The body-mountable device could detect the property of the probe and such a detected property could be used to determine the presence or status of the tumor. As an illustrative example, FIG. 4A shows a tumor 420 within a body and a portion of vasculature 410 proximate the tumor 420. Blood flows into 421a and out of 411b the portion of vasculature 410. The portion of vasculature 410 is fenestrated (i.e., has breaks in its walls); as a result, cells, macromolecules, probes, or other contents of the blood flowing into 421a the portion of vasculature 410 can leave the portion of vasculature 410 and interact with the tumor 410. For instance, and as illustrated in FIG. 4A, a probe 400 has left the portion of vasculature 410 and entered the tumor 420.

Figure 4B:
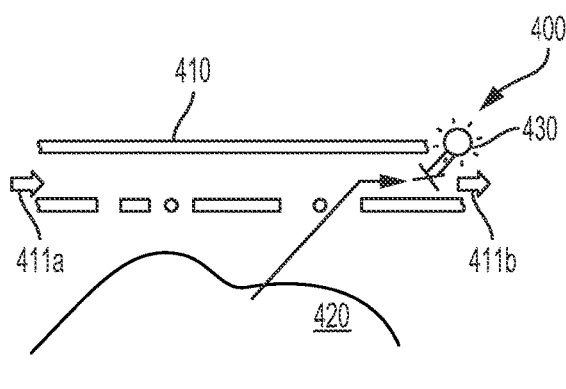
FIG. 4B is an illustration of the probe of FIG. 4A leaving the tumor while associated with a cell of the tumor and entering the portion of vasculature, in accordance with an example embodiment.

As illustrated in FIG. 4A, the probe 400 includes a fluorophore 430 and a quencher 440 that is configured to quench the fluorescence of the fluorophore 430. After the probe 400 enters the tumor, the quencher 440 could be prevented from quenching the fluorophore 430 and/or a degree of quenching of the fluorophore 430 by the quencher 440 could be decreased. As a result, the fluorescence intensity of the fluorophore 430, and thus of the probe as a whole, could be increased, and such an increased fluorescence intensity could be detected by a body-mountable device if the probe travels to a portion of superficial vasculature proximate such a device. This is illustrated by way of example in FIG. 4B, wherein the quencher 440 has been cleaved from the probe 400. The probe 400 then leaves the tumor and enters the portion of vasculature 410.

As noted above, a body-mountable device could detect the presence and/or one or more properties of a probe as described herein, and such a detected presence or property could be used to determine a presence or status of a tumor in a body. Such a determined presence or status (e.g., a determined tumor type, size, stage, degree or rate of metastasis) could be used to determine a course of treatment. For example, a course of chemotherapy, a surgical intervention, or some other treatments could be determined and executed in response to determining that a tumor is present and/or that such a tumor is of a certain type, is metastasizing, or has some other status. Additionally or alternatively, a tumor could be imaged (e.g., using an X-ray computerized tomography scanner, using a magnetic resonance imager, using a gamma camera, using a fluorescence imager) in response to determining that the tumor is present using a probe and body-mountable (or otherwise configured) device as described herein. In such examples, the probe could function as a contrast for the imaging, e.g., the probe could include an X-ray contrast agent (e.g., an iodine or barium compound), an MR contrast agent (e.g., particles of gadolinium), a positron emitter, a fluorophore, or some other contrast agent to facilitate imaging of the tumor.

As noted above, a probe could interact with a tumor in a variety of ways such that a property of the probe is changed, such that the probe is released from the tumor, or such that some other process occurs that can be detected by a body-mountable device if the probe travels, through the circulation, to a portion of subsurface vasculature that is observable by the body-mountable device. Such changes (e.g., cleavage of elements of the probe, denaturation of elements of the probe, changes in conformation or geometry of the probe, addition of elements to the probe, association of the probe with a tumor cell) could be caused by exposure to the environment of a tumor. For example, a pH level, an oxygen saturation, a concentration of lactic acid, a similarity between the tumor environment and the blood (e.g., due to the tendency for the vasculature of a tumor to be fenestrated and/or due to the enhanced permeability and retention effect), a presence or concentration of a protease, protein, or other substance, or some other property of the environment of a tumor that is characteristic of the tumor. A probe could be sensitive to such factors that are common across a variety of tumor types (e.g., a decreased pH within a tumor relative to other tissues of a body) and/or to factors that are specific a particular tumor type or set of tumor types (e.g., the presence of a protease that is characteristic of a particular variety of cancer).

Figure 5:
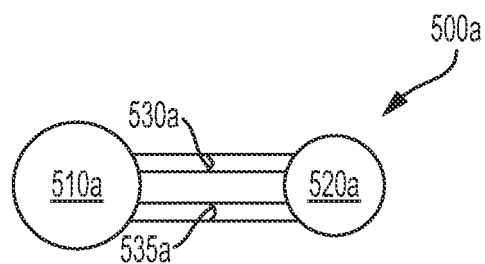
FIG. 5 is a schematic diagram of elements of a probe, in accordance with an example embodiment.

In order to control the specificity of a probe to tumors and/or to a particular tumor type, the probe could only change a property, associate with cells, be released from a probe aggregate or other anchoring element, or otherwise experience some change in response to exposure to multiple factors that are characteristic of tumors and/or a particular tumor type. For instance, cleavage of the probe from an anchor and/or cleavage of some other element of a probe could be dependent on exposure to multiple factors (e.g., a pH within a specific range and a protease, or two different proteases). As an example, FIG. 5 illustrates first 510a and second 520a elements of a probe 500a. The first and second elements 510a, 520a are connected by first 530a and second 535a linking elements (e.g., first and second peptides) that are configured to be cleaved by respective different factors of a tumor environment (e.g., first and second different proteases that are both characteristic of a particular tumor type). The first and second elements 510a, 520a could be, respectively, a fluorophore and a quencher, a probe and an anchoring element, or some other combination of elements. The first and second elements 510a, 520a could be separated if the probe 500a is exposed to both of the different factors such that the first 530a and second 535a linking elements are both cleaved. A probe could be configured to be sensitive to more than two factors, to cleave (or to change in some other way) in response to the presence of at least one of a set of factors (e.g., by assembling the first 530a and second 535a linking elements in series, rather than in parallel as shown in FIG. 5) or according to some other combination or permutation of factors according to an application.

Figure 6A:
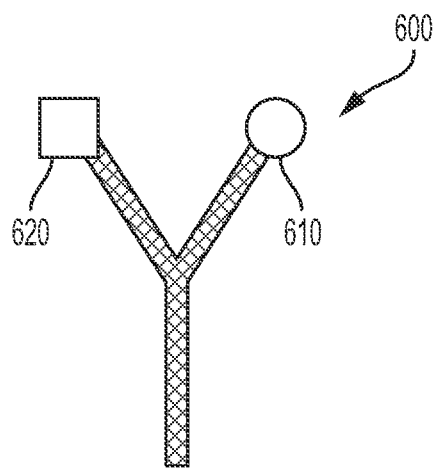
FIG. 6A is a schematic diagram of elements of a probe, in accordance with an example embodiment.

As noted above, first and second elements of a probe could be cleaved apart to release the probe, to change a property of the probe (e.g., by cleaving off a quencher, a fluorophore, or some other detectable element). Alternatively, a property of a probe could be changed by changing a conformation or geometry of elements of the probe, e.g., to increase a distance between a quencher and a fluorophore to decrease a degree of quenching of the fluorophore by the quencher. As an example, FIG. 6A shows a probe 600 that includes a fluorophore 610 and a quencher 620. A fluorescence intensity of the fluorophore 620 is related to the distance between the fluorophore 610 and a quencher 620 such that the fluorescence intensity of the fluorophore 610 increases as the distance to the quencher 620 increases.

Figure 6B:
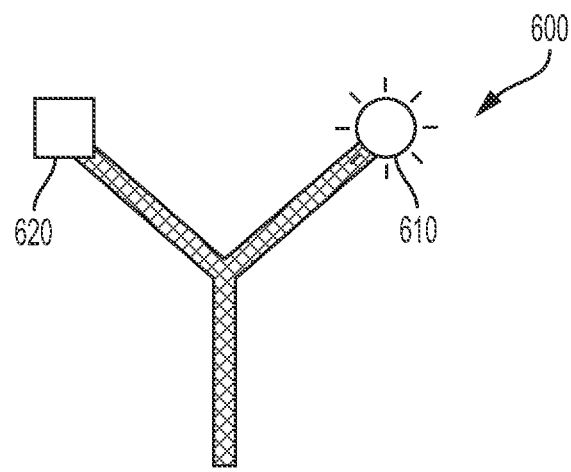
FIG. 6B is a schematic diagram of the elements of the probe of FIG. 6A after interacting with a tumor, in accordance with an example embodiment.

Thus, exposure to a tumor environment, or some other interaction between a tumor and the probe 600, could change (e.g., increase) the fluorescence intensity of the probe 600 by changing the distance (e.g., increasing the distance) between the fluorophore 610 and the quencher 620. This is illustrated by way of example in FIG. 6B, wherein the probe 600 has changed its geometry such that the distance between the fluorophore 610 and the quencher 620 is increased relative to the configuration of the probe 600 that is shown in FIG. 6A. As a result, the fluorescence intensity of the fluorophore 610 (and thus of the probe 600) is increased.

Such an increased (or decreased) distance between elements of a probe could be caused by changes in the structure of a protein or other elements of the probe, e.g., the cleavage of a tether between elements of the probe, a change in secondary or tertiary structure of a protein of the probe, or some other change. Such changes in the structure of a probe could be due to a substance (e.g., a protein, an antibody, an aptamer) that is present in a tumor binding to the probe (e.g., to cause a change in conformation of an antibody or other elements of the probe), a reaction between the probe and a substance (e.g., a protease, an enzyme) that is present in the tumor such that the reaction denature, lyses, cleaves, or otherwise alters the structure of a protein or other element of the probe, or some other mechanism.

A probe as described herein could have multiple properties that are indicative of whether the probe has interacted with a tumor. For example, the probe could have a fluorescence intensity at a number of different wavelengths (e.g., corresponding to multiple different fluorophores and/or quenchers of the probe) where the fluorescence intensity at each wavelength has a value that is related to whether the probe interacted with a tumor and/or whether the probe interacted with a tumor of a particular type. For instance, a probe could include a first fluorophore having a first fluorescence intensity that is changed in response to exposure to a pH level characteristic of the tumor environment of a variety or tumor types and a second fluorophore having a second fluorescence intensity that is changed in response to exposure to a protease that is characteristic of the tumor environment of a particular tumor type. In such an example, detection of the first and second fluorescence intensities (e.g., by illuminating the probe with light at first and second wavelengths and/or detecting light emitted from the probe at first and second wavelengths) could allow for determination of whether a tumor is present in a body and/or whether such a tumor is of the particular type.

Further, a property of a probe that is indicative of whether the probe has interacted with a tumor could be related to some property of the interaction and/or of the tumor such that the property of the interaction and/or of the tumor could be determined based on the detected property of the probe. For example, a degree of reduction or increase of the fluorescence intensity of a probe from a baseline level could be related to the level of pH in a tumor, a size of the tumor, an amount of time the probe interacted with the tumor (e.g., an amount of time between the probe being absorbed into or otherwise exposed to the tumor and the probe exiting the tumor), a degree of perfusion of the tumor, or some other property of the tumor and/or of the interaction of the probe with the tumor. The probe could be configured in a variety of different ways to provide such a property. For instance, the probe could include a plurality of fluorophores that are configured to be cleaved off of the probe or to otherwise exhibit a reduction in the overall fluorescence intensity of the probe as a result of interaction with the probe (e.g., as a result of exposure to a protease in the tumor, or as a result of exposure to a pH within the tumor). As the probe continuous to interact with the tumor, the overall fluorescence intensity of the probe could decrease as more of the fluorophores are cleaved off or otherwise reduce their fluorescence intensity.

In order to determine whether a probe has interacted with a tumor, the probe could have a first detectable property (e.g., a first fluorescence intensity at a first excitation and/or emission wavelength) that is indicative of whether the probe has interacted with a tumor and a second detectable property (e.g., a second fluorescence intensity at a second excitation and/or emission wavelength, a magnetic field of a magnetic nanoparticle) that is substantially independent of whether the probe has interacted with the tumor. The first and second properties could be detected and used to determine whether the probe has interacted with a tumor. Further, the detectable property that is substantially independent of whether the probe has interacted with a tumor could be used to normalize the detectable property that is indicative of whether the probe has interacted with the tumor, e.g., to allow a duration of time the probe interacted with the tumor, a pH level or other value of a property of the tumor, or some other property of the tumor and/or of the interaction between the tumor and the probe to be determined.

Figure 7A:
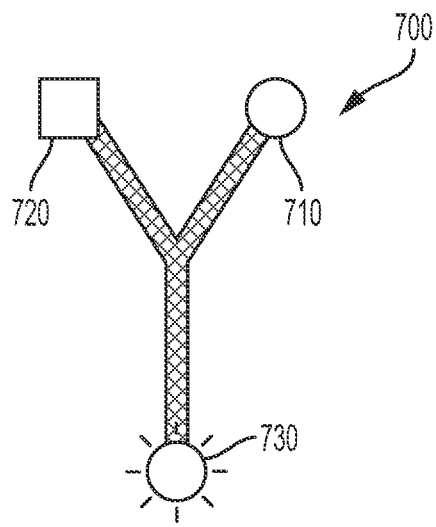
FIG. 7A is a schematic diagram of elements of a probe, in accordance with an example embodiment.

As an illustrative example, FIG. 7A shows a probe 700 that includes a first fluorophore 710 and a quencher 720. A first fluorescence intensity of the first fluorophore 710 is related to the distance between the first fluorophore 710 and a quencher 720 such that the first fluorescence intensity of the first fluorophore 710 increases as the distance to the quencher 720 increases. The probe 700 also includes a second fluorophore 730 that has a second fluorescence intensity. Exposure to a tumor environment, or some other interaction between a tumor and the probe 700, could increase the first fluorescence intensity of the probe 700 by increasing the distance between the first fluorophore 710 and the quencher 720. This is illustrated by way of example in FIG. 6B, wherein the probe 700 has changed its geometry in response to interaction with a tumor such that the distance between the first fluorophore 710 and the quencher 720 is increased relative to the configuration of the probe 700 that is shown in FIG. 7A. As a result, the first fluorescence intensity of the first fluorophore 710 (and thus of the probe 700) is increased.

As shown in FIG. 7A, the probe 700 has not interacted with a tumor (e.g., has not been exposed to a pH, a protease, an oxygen content, or some other factor characteristic of an environment of the tumor) and so the first fluorescence intensity of the first fluorophore 710 is low while the second fluorescence intensity of the second fluorophore 730 is high. A body-mountable device could detect the probe 700 as depicted in FIG. 7A in a portion of subsurface vasculature by detecting the low first fluorescence intensity and high second fluorescence intensity; the detected first and second fluorescence intensities could then be used to determine that the probe 700 is present in the portion of subsurface vasculature and that the probe 700 has not interacted with a tumor. Based on such a determination, a presence or status of a tumor in the body could be determined.

Figure 7B:
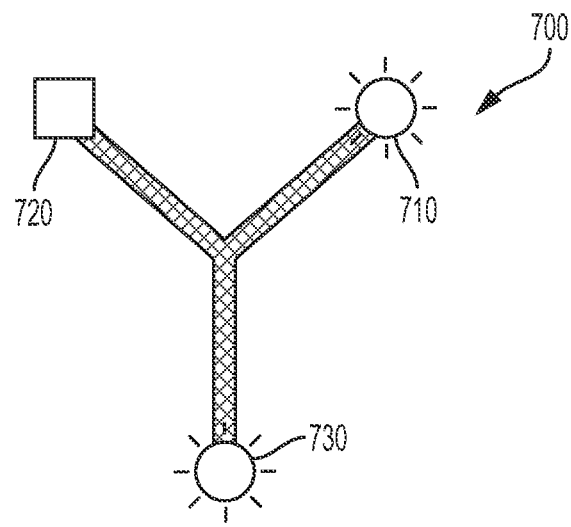
FIG. 7B is a schematic diagram of the elements of the probe of FIG. 7A after interacting with a tumor, in accordance with an example embodiment.

Alternatively, as shown in FIG. 7B, the probe 700 has interacted with a tumor (e.g., not been exposed to a pH, a protease, an oxygen content, or some other factor characteristic of an environment of the tumor) and so the first and second fluorescence intensities of the first fluorophore 710 and second fluorophore 730, respectively, are high. A body-mountable device could detect the probe 700 as depicted in FIG. 7B in a portion of subsurface vasculature by detecting the high first and second fluorescence intensities; the detected first and second fluorescence intensities could then be used to determine that the probe 700 is present in the portion of subsurface vasculature and that the probe 700 has interacted with a tumor. Based on such a determination, a presence or status of a tumor in the body could be determined. Further, the second fluorescence intensity could be used to normalize the first fluorescence intensity such that a property of the tumor (e.g., a concentration of a protease, a pH level, a level of perfusion) and/or of the interaction between the probe 700 and the tumor (e.g., a duration of time during which the probe was exposed to the tumor) could be determined based on the normalized first fluorescence intensity.

III. EXAMPLE DETECTION OF PROBES IN SUBSURFACE VASCULATURE

As noted above, a probe can be introduced into the vasculature of a body and travel to a tumor within the body. Such a probe could then interact with the tumor and travel, via the vasculature, to a superficial portion of vasculature wherein the probe could be detected. The probe interacting with a tumor could include being selectively released from the tumor, associating with tumor cells of the tumor and metastasizing into the circulation with such cells, having a property that is altered by exposure to the tumor and/or otherwise indicative of the probe having interacted with the tumor, or otherwise interacting with the tumor. By traveling via the circulation to a portion of subsurface vasculature, the probe can be detected over a protracted period of time by a body-mountable device (e.g., a wrist mounted wearable device) that could be worn by a user and/or periodically (e.g., daily, for a period of a few minutes each day) mounted to a user's body (e.g., by placing the arm of the user proximate the body-mountable device such that a sensor of the device is proximate a portion of subsurface vasculature of the user's body) rather than less frequently by a CT scanner, an MRI device, or some other imaging or scanning equipment. Further, by interacting with tumor cells in a tumor, the probe can leverage factors present in the tumor microenvironment (e.g., a pH level, the enhanced permeability and retention effect) to increase the specificity of the probe. Additionally, such probes can be used to detect CTCs or other rare or infrequent events or analytes in lower doses than might be required to tag and detect such rare and/or infrequently present analytes directly after such analytes are present in the circulation.

Figure 8:
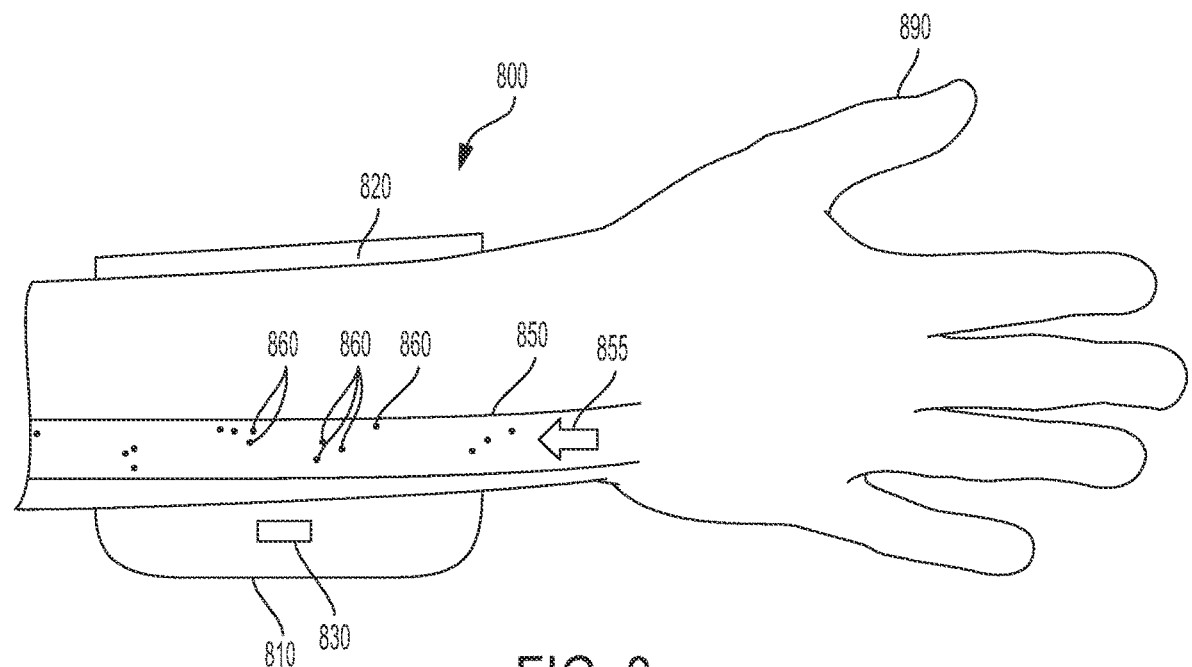
FIG. 8 is a side cross-sectional view of probes in a portion of subsurface vasculature and a device positioned proximate to the portion of subsurface vasculature, in accordance with an example embodiment.

As an illustrative example, FIG. 8 shows example probes 860 disposed in a blood vessel 850 (i.e., a portion of subsurface vasculature). In this example, disposed in blood vessel 850 are instances of the probe 860. The probes could be any type of probe as described elsewhere herein; further, multiple types of probe could be present in the blood vessel 850. The blood vessel 850 is located in an arm 890 and contains blood that is flowing (direction of flow indicated by the arrow 855). A wearable body-mountable device 800 includes a housing 810 mounted outside of or otherwise proximate to the blood vessel 850 by a mount 820 configured to encircle the arm 890. The wearable device 800 includes a sensor 830 (e.g., a light sensor, a light emitter, a magnetic sensor, and/or some other elements) that is configured to detect the probes 860 in the blood vessel 850 that are proximate the sensor 830. Such detection can include detecting that the probe(s) 860 are present in the blood vessel 850, determining a number, concentration, or amount of the probes 860 in the blood vessel 850 and/or determining properties of the probes 860 in the blood vessel 850.

The sensor 830 could be configured to detect a variety of physical properties in order to detect the presence of the probes 860 and/or to detect one or more properties of individual probes 860 (e.g., a property of an individual probe that is indicative of whether the individual probe has interacted with a tumor). This could include detecting physical variables that are related to fluorophores, chromophores, dyes, Raman dyes, fluorescent nanodiamonds, fluorescent quantum dots, magnetic nanoparticles, or other detectable elements of the probes 860. The sensor 830 could be configured to detect such physical variables in such a way that individual probes 860 can be detected. This could include detecting the fluorescence intensity of a single probe and/or a fluorophore of a single probe, detecting a magnetic field produced by a magnetic nanoparticle of a single probe, or detecting some other detectable element of a single probe 860 in the blood vessel 850. Additionally or alternatively, the sensor 830 could be configured to detect properties of a population of probes 860 in the blood vessel 850. This could include detecting the aggregate fluorescence intensity of a population of the probes 860 in the blood vessel 850, detecting a T1 time, a T2* time, or some other magnetic resonance time constant of hydrogen atoms in the blood that is related to magnetic fields produced by a population of magnetic nanoparticles of the probes, or detecting some other aggregate property of probes 860 in the blood vessel 850.

In examples wherein the probes 860 have a detectable optical property (e.g., a color, an emission spectrum, an excitation spectrum, an absorption spectrum, a Stokes shift), the sensor 830 could be configured to detect such an optical property. The sensor 830 could include a light sensor (e.g., a photodiode, a phototransistor, an avalanche photodiode, a CCD sensor, a camera, a spectrometer) that is configured to detect the intensity, polarization, wavelength, spectral content, degree of coherence, or other properties of light received from the blood vessel 850, e.g., light emitted from probes 860 within the blood vessel 850. The sensor 830 could be configured to detect such properties of light received from a relatively wide field of view encompassing a portion of the blood vessel 850 (e.g., to detect multiple probes 860) and/or could include one or more sensing elements (e.g., pixels of a camera) configured to detect properties of light received from a sufficiently narrow field of view that individual probes 860 and/or properties thereof could be detected. Further, the sensor 830 could include one or more light emitters configured to illuminate the blood vessel 850, e.g., to excite a fluorophore of the probes 860, to interrogate a color or absorbance spectrum of the probes 860, or to interrogate some other optical property of the probes 860.

In examples wherein the probes 860 have a detectable magnetic property (e.g., a magnetic moment, a magnetic relaxation time, a coercivity), the sensor 830 could be configured to detect such a magnetic property. The sensor 830 could include a Hall sensor, an atomic optical magnetometer, a multipass atomic magnetometer, a spin exchange relaxation-free magnetometer, or some other element(s) configured to detect a magnitude and/or direction of a magnetic field proximate the blood vessel 850. The sensor 830 could detect a magnetic field produced by a magnetic nanoparticle or other magnetic element of the probes 860 that is permanently magnetized, that becomes magnetized spontaneously, or that has been magnetized (e.g., by a permanent magnet or electromagnet of the wearable device 800). Additionally or alternatively, the wearable device 800 could generate an alternating magnetic field and the sensor 830 could detect the probes 860 by detecting magnetic fields produced by the probes 860 in response to exposure to the alternating magnetic field (e.g., alternating magnetic fields at a harmonic frequency of the alternating field generated by the wearable device 800).

In some examples, the sensor 830 could indirectly detect a magnetic field produced by the probes 860, e.g., by detecting a change in the magnetic resonance properties of atoms in the blood. This could include polarizing the magnetic spins of atoms in the blood (e.g., hydrogen atoms) using, e.g., a high-strength magnet or electromagnet of the wearable device 800, rotating the polarized atoms using coils of the wearable device 800 (e.g., emitting pi pulses, ½ pi pulses, or other pulses or patterns of pulses used in nuclear magnetic resonance and/or magnetic resonance imaging), and operating the sensor 830 to detect magnetic fields produced by the atomic spins as they relax in a manner related to magnetic fields produced by the probes 860.

A presence or status of a tumor in the body could be determined based on a detected presence and/or properties of probes 860 in the blood vessel 850. Such a determination could be based on the properties of the probes 860. For example, if the probes 860 are configured to be released from a tumor subsequent to being absorbed into the tumor or to associate with tumor cells and to leave the tumor with associated tumor cells when the tumor cells metastasize, the presence of a tumor, a size of a tumor, a type of a tumor (e.g., if the probes 860 are configured to selectively associate with and/or be released from a particular tumor type), a rate or degree of metastasis of a tumor, or some other information about the presence or status of a tumor could be determined based on an amount of detected probes 860, a rate or frequency at which the probes 860 are detected, and/or a timing of detection of the probes 860 relative to, e.g., introduction of the probes 860 into the body.

Additionally or alternatively, if the probes 860 have a property that is indicative of the probes having interacted with a tumor, the presence of a tumor, a size of a tumor, a degree of perfusion of a tumor, a type of a tumor (e.g., if the property of the probes 860 is indicative of interaction with a particular tumor type), a property of the environment of a tumor (e.g., a pH level in the tumor), a property of the interaction between a tumor and the probe(s) 860 (e.g., a duration of time during which a probe was exposed to a tumor), or some other information about the presence or status of a tumor could be determined based on a measured property of detected probes 860.

In some examples, probes as described herein could include magnetic elements (e.g., nanoparticles of superparamagnetic iron oxide). As noted above, magnetic fields produced by such magnetic elements could be detected by a body-mountable device and used to determine the presence or other properties of the probes in a portion of subsurface vasculature and/or to determine the presence or status of a tumor in a body. Additionally or alternatively, such magnetic elements (e.g., magnetic nanoparticles) could be used to collect probes in a portion of subsurface vasculature by exerting a magnetic force on the probes. Such probes could be collected to improve the detection of the presence and/or other properties of the probes by, e.g., increasing a magnitude of a magnetic field produced by the probes in the portion of subsurface vasculature, by increasing the intensity of a light (e.g., a fluorescence light) produced by the probes, or otherwise improving the detection of some detectable property of the probes in the portion of subsurface vasculature by increasing the number or concentration of the probes in the portion of subsurface vasculature.

Figure 9:
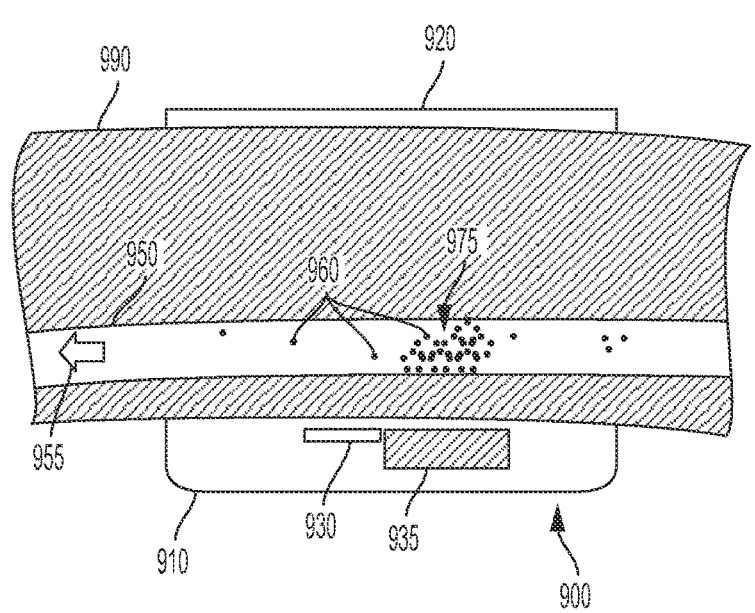
FIG. 9 is a side cross-sectional view of nanoparticles in a portion of subsurface vasculature and a device positioned proximate to the portion of subsurface vasculature during a first period of time, in accordance with an example embodiment.

FIG. 9 illustrates example probes 960 as described elsewhere herein. The probes 960 include magnetic nanoparticles and are disposed in a blood vessel 950 (i.e., a portion of subsurface vasculature). The blood vessel 950 is located in an arm 990 and contains blood that is flowing (direction of flow indicated by the arrow 955). A wearable body-mountable device 900 includes a housing 910 mounted outside of the blood vessel 950 by a mount 920 configured to encircle the arm 990. The wearable device 900 includes a sensor 930 disposed in the housing 910 and configured to detect a detectable property of the probes 960 in order to, e.g., determine the presence, location, or other properties of the probes 960. Such properties of the probes 960, detected using the sensor 930, could be used to determine a presence or status of a tumor in the body that comprises the arm 990.

The wearable device 900 additionally includes a magnetic flux source 935 (e.g., a permanent magnet, an electromagnet) configured to exert an attractive magnetic force on the magnetic nanoparticles of the probes 960 such that at least some of the probes 960 in the blood vessel 950 are collected proximate the magnetic flux source 935. Such a magnetic flux source could be considered a collection magnet. The magnetic flux source 935 could additionally be configured to magnetize the magnetic nanoparticles of the probes 960, to polarize magnetic spins of nuclei (e.g., hydrogen nuclei) in the blood, or to provide some other functions.

As shown in FIG. 9, the magnetic flux source 935 is exerting an attractive magnetic force to attract the probes 960 to form a bolus 975 of collected probes 960. The sensor 930 could be configured to detect the presence, amount, concentration, or other properties of the probes 960 collected in the bolus 975 when the magnetic flux source 935 is exerting an attractive magnetic force on the probes 960. Additionally or alternatively, the magnetic flux source 935 could be configured and/or operated to, after exerting a magnetic force sufficient to collect the bolus 975 of probes 960, exert a lesser magnetic force (e.g., to exert substantially no magnetic force) on the probes 960 such that the bolus 975 is released from the proximity of the magnetic flux source 935 and flows within the blood vessel 950 to a downstream location, e.g., past the sensor 930. The sensor 930 could then operate to detect a light emitted by the probes 960 (e.g., in response to illumination emitted from the sensor 930), a magnetic field produced by the probes 960 and/or some other physical variable related to the probes 960.

IV. EXAMPLE BODY-MOUNTABLE DEVICES

Body-mountable devices as described herein can be configured to be mounted to an external body surface of a person and to enable a variety of applications and functions including the detection of probes as described elsewhere herein that are disposed in the body of the person (e.g., disposed in a portion of subsurface vasculature of the person) and that have a property (e.g., a fluorescence intensity, an amount or number of the probe that is present in a portion of vasculature, a rate, frequency, or timing of the probe being present in a portion of vasculature) that is related to the presence or status of a tumor in the body of the person. Such devices could include one or more sensors configured to detect a light, a magnetic field, or some other physical variable that is related to the presence of one or more probes in a portion of subsurface vasculature proximate the sensor(s) and/or to detect a property (e.g., a fluorescence intensity, an emission spectrum) of such one or more probes.

In some examples, the probes could include magnetic nanoparticles and such devices could include one or more magnetic flux sources configured to collect the probes in a portion of subsurface vasculature and/or to provide some other functionality (e.g., to polarize the magnetic spins of atomic nuclei in a body, to magnetize the magnetic nanoparticles). Such body-mountable devices could enable a variety of applications, including detecting properties of the probes in order to, e.g., determine a presence or status of a tumor in the body of a person, to detect other physiological information about a person (e.g., heart rate), to indicate such determined information or other information to the person (e.g., using a vibrator, a screen, a beeper), or other functions.

A wearable body-mountable device 1000 (illustrated in FIG. 10) can be configured to detect probes disposed in a wearer's body (e.g., disposed in portions of subsurface vasculature proximate the device 1000) and to exert a magnetic force to collect such probes that include magnetic nanoparticles. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature or other targets or elements of the body of the wearer are easily observable, the qualification of which will depend on the type of detection system used. The device may be placed in close proximity to the skin or tissue. A mount 1010, such as a belt, wristband, ankle band, etc. can be provided to mount the device at, on or in proximity to the body surface. The mount 1010 may prevent the wearable device from moving relative to the body to reduce measurement error and noise. In one example, shown in FIG. 10, the mount 1010, may take the form of a strap or band 1020 that can be worn around a part of the body. Further, the mount 1010 may be an adhesive substrate for adhering the wearable device 1000 to the body of a wearer.

A housing 1030 is disposed on the mount 1010 such that it can be positioned on the body. A contact surface 1040 of the housing 1030 is intended to be mounted facing to the external body surface. The housing 1030 may include a magnetic flux source 1055 for producing a magnetic field sufficient to collect probes that are disposed in the body of the wearer and that include magnetic nanoparticles. The housing 1030 may additionally include a sensor 1050 for detecting magnetic fields, light, or other phenomena produced by such probes disposed in the body of the wearer. The housing 1030 could be configured to be water-resistant and/or water-proof.

The magnetic flux source 1055 is configured to produce a magnetic field sufficient to collect magnetic nanoparticles disposed proximate to the magnetic flux source 1055 in an environment of interest, e.g., a portion of subsurface vasculature of a wearer. For example, the magnetic flux source 1055 could be configured to produce a magnetic field having a magnitude of several hundred Gauss (e.g., greater than approximately 100 Gauss) at a distance of approximately 1 centimeter from the contact surface 1040 (e.g., a distance within which a portion of subsurface vasculature containing the nanoparticles may be located when the device 1000 is mounted to a body). The magnitude of the magnetic field produced by the magnetic flux source 1055 and the dimensions of the magnetic flux source 1055 (e.g., the length of the magnetic flux source 1055 in a direction aligned with a direction of the portion of subsurface vasculature) could be specified such that magnetic nanoparticle-containing probes flowing in the body proximate to the magnetic flux source 1055 are collected proximate the magnetic flux source 1055.

The magnetic flux source 1055 could be configured to collect such probes and/or to release such collected probes, e.g., to facilitate extraction of the collected probes from the body, to provide a higher-magnitude optical, magnetic, or other type of signal for the sensor 1050 to detect, or according to some other application. The magnetic flux source 1055 could include one or more electromagnets, permanent magnets, or other magnetic producing elements. Further, the magnetic flux source 1055 could be configured and/or operated to change a magnetic field produced by the magnetic flux source 1055, e.g., to reduce a magnitude of a produced magnetic field that is detected by a magnetometer of the sensor 1050, to reduce an inhomogeneity of the magnetic field proximate a magnetometer of the sensor 1050 that is caused by the magnetic flux source 1055, to release collected probes such that the collected probes can be transported, by a blood flow, past the sensor 1030, or according to some other application. This could include changing a current applied to an electromagnet of the magnetic flux source 1055, mechanically actuating an electromagnet, permanent magnet, or other flux producing element of the magnetic flux source 1055, or performing some other operation(s).

Note that the magnetic flux source 1055 could be configured to provide some other functionality, e.g., to magnetize the magnetic nanoparticles of the probes or to polarize the magnetic spins of atomic nuclei such that the magnetic field in the environment of such atomic nuclei (e.g., a magnetic field produced by a magnetized nanoparticle of a probe proximate such atomic nuclei) could be detected (e.g., by the magnetometer 850 detecting time-varying magnetic and/or electromagnetic fields produced by such atomic nuclei through nuclear magnetic resonance).

The sensor 1050 is configured to detect the presence, number, concentration, location, or other properties of probes as described elsewhere herein that are located in an environment of interest, e.g., a portion of subsurface vasculature of a wearer. The sensor 1050 could include a light sensor configured to detect an intensity, wavelength, spectral content, polarization, or other properties of light emitted from such probes, e.g., light reflected or scattered by a chromophore, dye, or Raman dye of a probe or light fluorescently emitted from a fluorescent organic compound, a fluorescent defect in a nanodiamond, or some other fluorescent element of a probe. Further, sensor 1050 could include one or more light emitters configured to emit light having a specified intensity, polarization, wavelength, spectral content, or some other specified property in order to optically interrogate the a probe, e.g., to illuminate the probe or to excite a fluorophore of the probe. The sensor 1050 could include a magnetometer that is configured to detect a direction, magnitude, property of change over time, or some other property of the magnetic fields produced by magnetic nanoparticles or other magnetic elements of a probe. Such a magnetometer could be configured to detect time-varying magnetic fields across a specified range of frequencies, e.g., less than several kilohertz (e.g., a spin-exchange relaxation-free atomic magnetometer, a multi-pass scalar atomic magnetometer), at a particular frequency (e.g., a radio-frequency atomic magnetometer tuned to a frequency of interest, e.g., an expected frequency of precession of magnetic spins of atomic nuclei in a magnetic field).

The wearable device 1000 may also include a user interface 1090 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 1090 may include a display 1092 where a visual indication of the alert or recommendation may be displayed. The display 1092 may further be configured to provide an indication of the presence or properties of one or more detected probes and/or a presence or status of a tumor in the body of the wearer.

Figure 10:
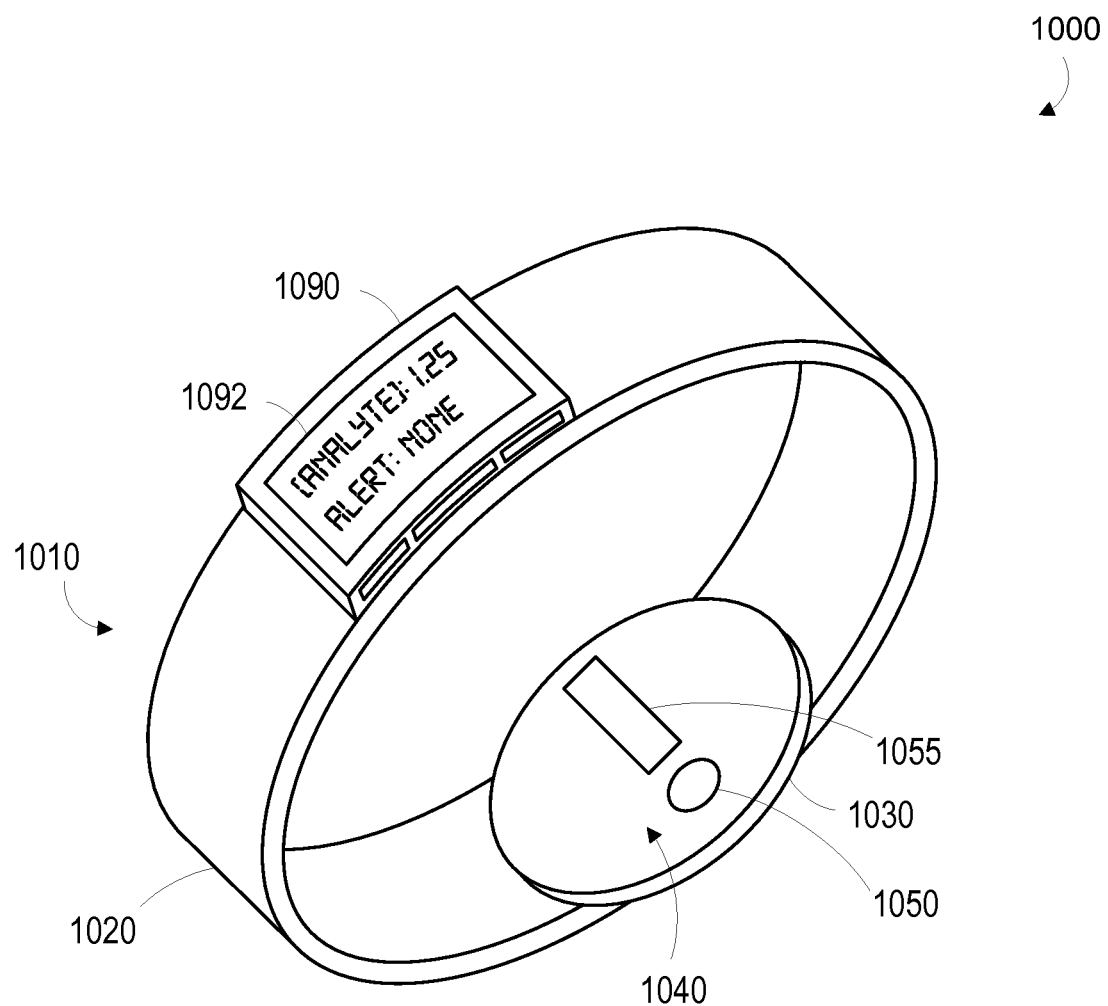
FIG. 10 is perspective view of an example device.

Note that example devices herein are configured to be mounted to a wrist of a wearer. However, the embodiments described herein could be applied to other body parts (e.g., an ankle, a thigh, a chest, a forehead, a thigh, a finger), or to detect probes in other environments. Further, while the body-mountable device 1000 of FIG. 10 is illustrated as a wearable device that is configured to be mounted to an external body surface of a person and to be worn by a person, body-mountable devices as described herein could take other forms. For example, body-mountable devices could include hand-held devices configured to be manually mounted to an external body surface of a person (e.g., a wrist surface) such that a sensor of the body-mountable device is proximate to a portion of subsurface vasculature beneath the external body surface. Additionally or alternatively, a body-mountable device may be a desktop or otherwise configured device that a body part can be brought into contact with (e.g., against which an arm may be positioned) such that a sensor of the body-mountable device is proximate to a portion of subsurface vasculature beneath an external body surface of the body part.

The term "body-mountable device," as used in this disclosure, refers to any device that is capable of being mounted at, on or in proximity to a body surface and/or a device (e.g., a desktop device) that a body part (e.g., an arm) can be brought into contact with such that a surface of the body part is mounted at, or in proximity to, the device. In order to take in vivo measurements in a non-invasive manner from outside of the body, the body-mountable device may be positioned on a portion of the body where subsurface vasculature or other targets or elements of the body of the wearer are easily observable, the qualification of which will depend on the type of detection system used. Additionally or alternatively, a portion of the body may be positioned on or within the body-mountable device such that subsurface vasculature or other targets or elements of the body of the wearer are easily observable Body-mountable devices and other embodiments as described herein can include a variety of components configured in a variety of ways. Devices described herein could include electronics including a variety of different components configured in a variety of ways to enable applications of the body-mountable device. The electronics could include controllers, amplifiers, switches, display drivers, touch sensors, wireless communications chipsets (e.g., Bluetooth radios or other radio transceivers and associated baseband circuitry to enable wireless communications between the body-mountable device and some other system(s)), or other components. The electronics could include a controller configured to operate one or more magnetic flux sources and/or sensors to collect and/or release probe(s) in a portion of subsurface vasculature, to detect a light, a magnetic field, or some other physical variable relating to a probe in a portion of subsurface vasculature, and/or to detect some other properties of a user or to perform some other functions. The controller could include a processor configured to execute computer-readable instructions (e.g., program instructions stored in data storage of the body-mountable device) to enable applications of the body-mountable device. The electronics can include additional or alternative components according to an application of the body-mountable device.

Body-mountable devices as described herein could include one or more user interfaces. A user interface could include a display configured to present an image to a user and to detect one or more finger presses of a user on the interface. The controller or some other component(s) of the electronics could operate the user interface to provide information to a user or other user of the device and to enable the user or other user to affect the operation of the body-mountable device, to determine some property of the body-mountable device and/or of the user of the body-mountable device (e.g., a presence or status of a tumor in the body of a user of the body-mountable device and/or some other health state of the user), or to provide some other functionality or application to the user. As one example, the user could press an indicated region of the user interface to indicate that an amount of probes have been introduced into the body of the user. Other indicated information, changes in operation of the body-mountable device, or other functions and applications of the user interface are anticipated.

Note that the embodiments illustrated in the Figures are illustrative examples and not meant to be limiting. Alternative embodiments, including more or fewer components in alternative configurations are anticipated. A body-mountable device could include multiple housings or other such assemblies each containing some set of components to enable applications of such a body-mountable device. For example, a body-mountable device could include a first housing within which are disposed one or more magnetic flux sources configured to collect magnetic nanoparticle-containing probes that are disposed in the user's body (e.g., within portions of subsurface vasculature of the user) and one or more sensor configured to detect such collected probes (e.g., to detect such probes while the probes are collected and/or subsequent to the release of such probes by the magnetic flux source). The body-mountable device could additionally include a second housing containing a user interface and electronics configured to operate the magnetic flux source(s) and sensor(s) and to present information to and receive commands from a user of the body-mountable device. A body-mountable device could be configured to perform a variety of functions and to enable a variety of applications. Body-mountable devices could be configured to operate in concert with other devices or systems; for example, body-mountable devices could include a wireless communication interface configured to transmit data indicative of one or more properties of the body of a user of the body-mountable device. Other embodiments, operations, configurations, and applications of a body-mountable device as described herein are anticipated.

Figure 11:
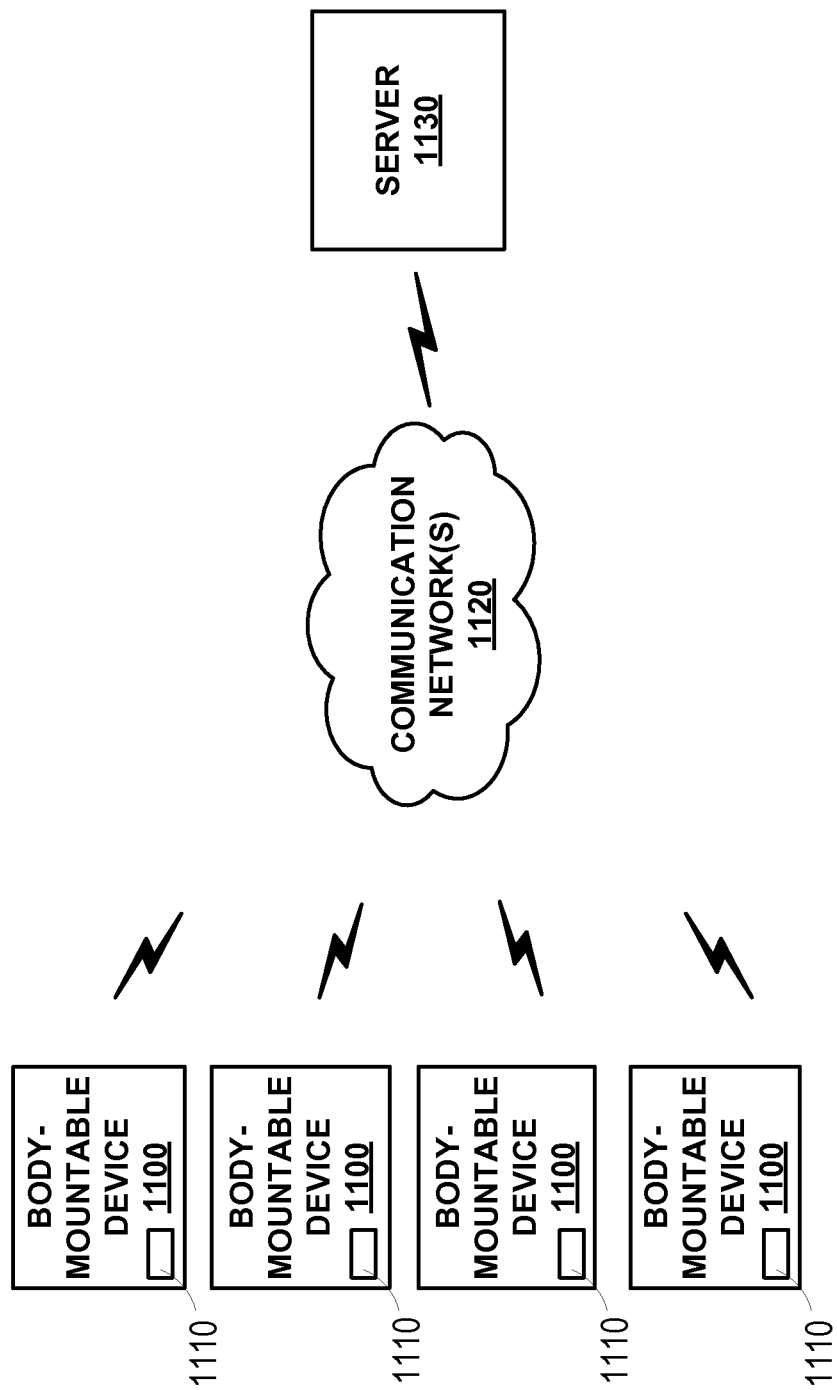
FIG. 11 is an illustration of a number of body-mountable devices in communication with a server, in accordance with an example embodiment.

FIG. 11 is a simplified schematic of a system including one or more body-mountable devices 1100. The one or more body-mountable devices 1100 may be configured to transmit data via a communication interface 1110 over one or more communication networks 1120 to a remote server 1130. In one embodiment, the communication interface 1110 includes a wireless transceiver for sending and receiving communications to and from the server 1130. In further embodiments, the communication interface 1110 may include any means for the transfer of data, including both wired and wireless communications. For example, the communication interface may include a universal serial bus (USB) interface or a secure digital (SD) card interface. Communication networks 1120 may be any one of may be one of: a plain old telephone service (POTS) network, a cellular network, a fiber network and a data network. The server 1130 may include any type of remote computing device or remote cloud computing network. Further, communication network 1120 may include one or more intermediaries, including, for example wherein the body-mountable device 1100 transmits data to a mobile phone or other personal computing device, which in turn transmits the data to the server 1130.

In addition to receiving communications from the body-mountable device 1100, such as a detected presence, concentration, or amount of a probe in a portion of subsurface vasculature, properties (e.g., fluorescence intensities) of such probes, a rate, frequency, or timing of the presence of such probes in a portion of subsurface vasculature and/or information determined therefrom (e.g., information about the presence or status of a tumor in the body of a user) or other collected physiological properties and data, the server may also be configured to gather and/or receive either from the body-mountable device 1100 or from some other source, information regarding a user's overall medical history, environmental factors and geographical data. For example, a user account may be established on the server for every user that contains the user's medical history. Moreover, in some examples, the server 1130 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a user's health state from a hospital or physician. Such information may be used in the server's decision-making process, such as recognizing correlations and in generating clinical protocols.

Additionally, the server may be configured to gather and/or receive the date, time of day and geographical location of each user of the device during each measurement period. Such information may be used to detect and monitor spatial and temporal spreading of diseases. As such, the body-mountable device may be configured to determine and/or provide an indication of its own location. For example, a body-mountable device may include a GPS system so that it can include GPS location information (e.g., GPS coordinates) in a communication to the server. As another example, a body-mountable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a user of the device and, at least in part, the detection of the presence or other properties of probes in the vasculature of a user and the indicated health state of the user. From this information, the server may be configured to derive an indication of the effectiveness of the drug or treatment. For example, a body-mountable device may be configured to detect the presence or status of a tumor by detecting properties of probes that are configured to selectively interact with the tumor and/or cells of the tumor. If a user is prescribed a drug intended to destroy tumor cells, but the server receives data from the body-mountable device indicating that, e.g., the number of tumor cells in the user's blood has been increasing over a certain number of measurement periods, the server may be configured to derive an indication that the drug is not effective for its intended purpose for this user.

Further, some embodiments of the system may include privacy controls which may be automatically implemented or controlled by the user of the device. For example, where a user's collected probe and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, users of a device may be provided with an opportunity to control whether or how the device collects information about the user (e.g., information about a user's medical history, social actions or activities, profession, a user's preferences, or a user's current location), or to control how such information may be used. Thus, the user may have control over how information is collected about him or her and used by a clinician or physician or other user of the data. For example, a user may elect that data, such as health state and detected probe data, collected from his or her device may only be used for generating an individual baseline and recommendations in response to collection and comparison of his or her own data and may not be used in generating a population baseline or for use in population correlation studies.

V. EXAMPLE ELECTRONICS PLATFORM FOR A DEVICE

Figure 12:
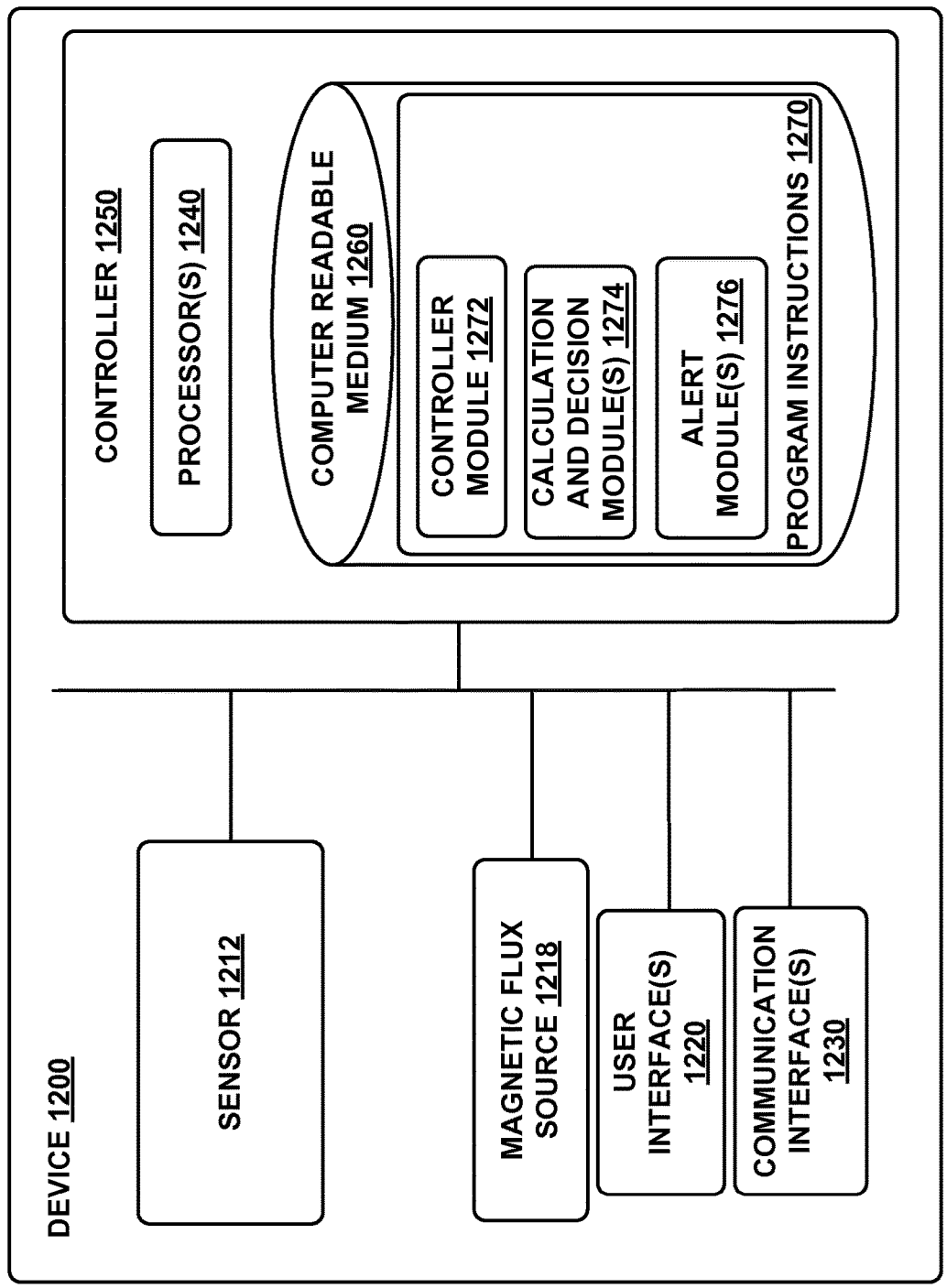
FIG. 12 is a block diagram of an example device.

FIG. 12 is a simplified block diagram illustrating the components of a device 1200, according to an example embodiment. Device 1200 may take the form of or be similar to one of the wearable and/or body-mountable devices 130, 800, 900, or 1000 shown in FIGS. 1, 8, 9, and 10. However, device 1200 may also take other forms, such as an ankle, waist, or chest-mounted device. Device 1200 also could take other forms. For purposes of illustration, device 1200 is described with reference to probes 860 in blood vessel 850, as shown in FIG. 8.

In particular, FIG. 12 shows an example of a device 1200 having a sensor 1212, a magnetic flux source 1218, a user interface 1220, communication interface 1230 for transmitting data to a remote system, and a controller 1250. The components of the device 1200 may be disposed on a mount or on some other structure for mounting the device to enable stable detection of one or more properties (e.g., a magnetic field, a light, or some other physical variable) related to the presence or other properties of a probe as described elsewhere herein that is present in a body of a user of the device 1200). For example, the device 1200 could include a structure configured for mounting the device 1220 to an external body surface where one or more portions of subsurface vasculature or other anatomical elements are readily observable.

Controller 1250 may be provided as a computing device that includes one or more processors 1240. The one or more processors 1240 can be configured to execute computer-readable program instructions 1270 that are stored in the computer readable data storage 1260 and that are executable to provide the functionality of a device 1200 described herein.

The computer readable medium 1260 may include or take the form of one or more non-transitory, computer-readable storage media that can be read or accessed by at least one processor 1240. The one or more computer-readable storage media can include volatile and/or non-volatile storage components, such as optical, magnetic, organic or other memory or disc storage, which can be integrated in whole or in part with at least one of the one or more processors 1240. In some embodiments, the computer readable medium 1260 can be implemented using a single physical device (e.g., one optical, magnetic, organic or other memory or disc storage unit), while in other embodiments, the computer readable medium 1260 can be implemented using two or more physical devices.

The sensor 1212 (e.g., a light sensor, a light emitter, a magnetic sensor, and/or some other elements) that is configured to detect the probes 860 in the blood vessel 850 that are proximate the sensor 830. Such detection can include detecting that the probe(s) 860 are present in the blood vessel 850, determining a number, concentration, or amount of the probes 860 in the blood vessel 850 and/or determining properties of the probes 860 in the blood vessel 850.

The sensor 1212 could be configured to detect a variety of physical properties in order to detect the presence of the probes 860 and/or to detect one or more properties of individual probes 860 (e.g., a property of an individual probe that is indicative of whether the individual probe has interacted with a tumor) that are located proximate the sensor 1212 in a body of a user of the device 1200 (e.g., within a portion of subsurface vasculature of the user). This could include detecting physical variables that are related to fluorophores, chromophores, dyes, Raman dyes, fluorescent nanodiamonds, fluorescent quantum dots, magnetic nanoparticles, or other detectable elements of the probes 860.

In examples wherein the probes have a detectable optical property (e.g., a color, an emission spectrum, an excitation spectrum, an absorption spectrum, a Stokes shift), the sensor 1212 could be configured to detect such an optical property. The sensor 1212 could include a light sensor (e.g., a photodiode, a phototransistor, an avalanche photodiode, a CCD sensor, a camera, a spectrometer) that is configured to detect the intensity, polarization, wavelength, spectral content, degree of coherence, or other properties of light received from the probes. Further, the sensor 1212 could include one or more light emitters configured to illuminate the probes and/or an environment that could contain the probes, e.g., to excite a fluorophore of the probes, to interrogate a color or absorbance spectrum of the probes, or to interrogate some other optical property of the probes.

In examples wherein the probes have a detectable magnetic property (e.g., a magnetic moment, a magnetic relaxation time, a coercivity), the sensor 1212 could be configured to detect such a magnetic property. The sensor 1212 could include a Hall sensor, an atomic optical magnetometer, a multipass atomic magnetometer, a spin exchange relaxation-free magnetometer, or some other element(s) configured to detect a magnitude and/or direction of a magnetic field. The sensor 1212 could include amplifiers, oscillators, ADCs, switches, filters, light emitters, light detectors, or other components configured to detect a magnetic field using one or more magnetic-field-sensitive elements of the sensor 1212. For example, the sensor 1212 could be a SERF magnetometer, a multipass scalar atomic magnetometer, a radio-frequency atomic magnetometer, or some other variety of atomic magnetometer that includes an alkali vapor cell (i.e., an enclosed volume containing a high-pressure, high-temperature vapor that includes alkali metal atoms) and the electronics could include a heater configured to vaporize the alkali metal in the vapor cell, a pump laser configured to emit circularly polarized light into the vapor cell to align the alkali metal atoms, a probe laser configured to probe the aligned alkali atoms with linearly polarized light, and a light detector configured to detect the change in orientation of the linearly polarized light that is related to the detected magnetic field. Other examples of magnetometers and electronics thereof are anticipated.

The device 1200 could include a bias coil (not shown) that is configured to produce a bias magnetic field to reduce a background magnetic field to which the sensor 1212 (e.g., a magnetometer of the sensor 1212) is exposed and/or to reduce an inhomogeneity of the magnetic field in an environment of interest (e.g., to cancel the effects of the Earth's magnetic field on the sensor 1212, to cancel the effects of the magnetic flux source 1218 on the sensor 1212) and/or to provide some other functionality. The bias coil could be driven according to a bias field magnitude determined based on an output of the sensor 1212, an output of some other magnetometer (not shown), an output of an accelerometer, gyroscope, or some other sensor, or based on some other consideration.

The magnetic flux source 1218 is configured to produce a magnetic field sufficient to collect magnetic nanoparticle-containing probes (e.g., by exerting an attractive magnetic force). The collected probes could be collected in a body (e.g., in a portion of subsurface vasculature) such that the presence or some other property of the probes could be detected by the sensor 1212. Additionally or alternatively, the magnetic flux source 1218 could subsequently release such collected probes such that the probes can be detected by the sensor 1212 (e.g., by being transported by a flow of blood within a portion of subsurface vasculature from the proximity of the magnetic flux source 1218 to the sensor 1212). The magnetic flux source 1218 could also be configured to magnetize magnetic nanoparticles of the probes (e.g., such that a magnetometer of the sensor 1212 could detect a magnetic field produced by the magnetized magnetic nanoparticles of the probes) and/or to polarize magnetic spins of atomic nuclei in an environment of interest such that the sensor 1212 can detect the presence or other properties of such probes by rotating the polarized magnetic spins of the atomic nuclei and detecting a time-varying magnetic field produced by precession of the rotated magnetic spins of the atomic nuclei. The magnetic flux source 1218 could be a permanent magnet and/or an electromagnet.

Note that a device could include a subset of the elements described here, e.g., a device could lack a magnetic flux source and/or some other combination of elements. Further, a device could include multiple of one or more illustrated elements. For example, a device could include multiple sensors 1212 configured to detect a light, a magnetic field, or some other physical variables at respective multiple different locations and/or in multiple different directions. In some examples, multiple illustrated elements of the device 1200 could be implemented as the same component and/or share some component(s) in common.

The program instructions 1270 stored on the computer readable medium 1260 may include instructions to perform any of the methods described herein. For instance, in the illustrated embodiment, program instructions 1270 include a controller module 1272, calculation and decision module 1274 and an alert module 1276.

The controller module 1272 may include instructions for operating the sensor 1212, magnetic flux source 1218, and/or some other components (e.g., one or more bias coils, pulse emitters, and/or excitation coils) to detect probes (e.g., to detect the presence, location, amount, or other properties) in a portion of subsurface vasculature proximate the sensor 1212 and/or to magnetically collect such probes (e.g., by exerting a magnetic force on magnetic nanoparticles of such probes).

The calculation and decision module(s) 1274 may include instructions for analyzing data generated by the sensor 1212 to determine information about probes in a body (e.g., by detecting the presence of such probes in a portion of subsurface vasculature and/or by detecting properties, of such probes, that are indicative of whether such probes have interacted with a tumor) or other information (e.g., health states) of a body of a user of the device 1200, such as a presence or status of a tumor in the body of the user. Calculation and decision module 1274 can additionally include instructions for analyzing the data to determine if a medical condition or other specified condition is indicated, or other analytical processes relating to the environment proximate to the device 1200.

In particular, if the probes are configured to be released from a tumor subsequent to being absorbed into the tumor or to associate with tumor cells and to leave the tumor with associated tumor cells when the tumor cells metastasize, the calculation and decision module(s) 1274 may include instructions for determining the presence of a tumor, a size of a tumor, a type of a tumor (e.g., if the probes 860 are configured to selectively associate with and/or be released from a particular tumor type), a rate or degree of metastasis of a tumor, or some other information about the presence or status of a tumor. Such determinations could be made based on an amount of the detected probes, a rate or frequency at which the probes are detected, and/or a timing of detection of the probes relative to, e.g., introduction of the probes into the body.

Additionally or alternatively, if the probes have a property that is indicative of the probes having interacted with a tumor, the calculation and decision module(s) 1274 may include instructions for determining the presence of a tumor, a size of a tumor, a degree of perfusion of a tumor, a type of a tumor (e.g., if the property of the probes is indicative of interaction with a particular tumor type), a property of the environment of a tumor (e.g., a pH level in the tumor), a property of the interaction between a tumor and the probe(s) (e.g., a duration of time during which a probe was exposed to a tumor), or some other information about the presence or status of a tumor. Such determinations could be made based on a measured property of detected probes.

The controller module 1272 can also include instructions for operating a user interface 1220. For example, controller module 1272 may include instructions for displaying data collected by the sensor 1212 and analyzed by the calculation and decision module 1274, or for displaying one or more alerts generated by the alert module 1276. Controller module 1272 may include instructions for displaying data related to probes in one or more portions of subsurface vasculature that have been detected using the sensor 1212 or some other detected and/or determined health state of a user. Further, controller module 1272 may include instructions to execute certain functions based on inputs accepted by the user interface 1220, such as inputs accepted by one or more buttons disposed on the user interface.

Communication interface 1230 may also be operated by instructions within the controller module 1272, such as instructions for sending and/or receiving information via a wireless antenna, which may be disposed on or in the device 1200. The communication interface 1230 can optionally include one or more oscillators, mixers, frequency injectors, etc. to modulate and/or demodulate information on a carrier frequency to be transmitted and/or received by the antenna. In some examples, the device 1200 is configured to indicate an output from the processor by modulating an impedance of the antenna in a manner that is perceivable by a remote server or other remote computing device.

The program instructions of the calculation and decision module 1274 may, in some examples, be stored in a computer-readable medium and executed by a processor located external to the device 1200. For example, the device 1200 could be configured to collect certain data, generated by the sensor 1212, regarding probes in a portion of subsurface vasculature in the body of the user and then transmit the data to a remote server, which may include a mobile device, a personal computer, the cloud, or any other remote system, for further processing. The remote server or other device could then use the transmitted data to determine a presence or status of a tumor in the body of the user. Information about such determinations could then be transmitted to the device 1200 and/or could be used in some other way (e.g., could be sent to a physician's computer).

The computer readable medium 1260 may further contain other data or information, such as medical and health history of a user of the device 1200, that may be useful in determining whether a medical condition or some other specified condition is indicated (e.g., in determining the presence or status of a tumor in the body of a user). Further, the computer readable medium 1260 may contain data corresponding to certain physiological parameter baselines, above or below which a medical condition is indicated. The baselines may be pre-stored on the computer readable medium 1260, may be transmitted from a remote source, such as a remote server, or may be generated by the calculation and decision module 1274 itself. The calculation and decision module 1274 may include instructions for generating individual baselines for the user of the device 1200 based on data collected over a period of time using the sensor 1212. Baselines may also be generated by a remote server and transmitted to the device 1200 via communication interface 1230. The calculation and decision module 1274 may also, upon determining that a medical or other emergency condition is indicated, generate one or more recommendations for the user of the device 1200 based, at least in part, on consultation of a clinical protocol. Such recommendations may alternatively be generated by the remote server and transmitted to the device 1200.

In some examples, detected information about probes in the vasculature of a user and/or and information determined therefrom about the presence or status of tumors in a user's body from a variety of different users or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular user's response to a drug or therapy. Based on this data, a physician or clinician may be able to tailor a drug treatment to suit an individual's needs.

In response to a determination by the calculation and decision module 1274 that a medical or other specified condition is indicated, the alert module 1276 may generate an alert via the user interface 1220. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication (e.g., a drug to destroy or disable circulating tumor cells).

VI. EXAMPLE METHODS

Figure 13:
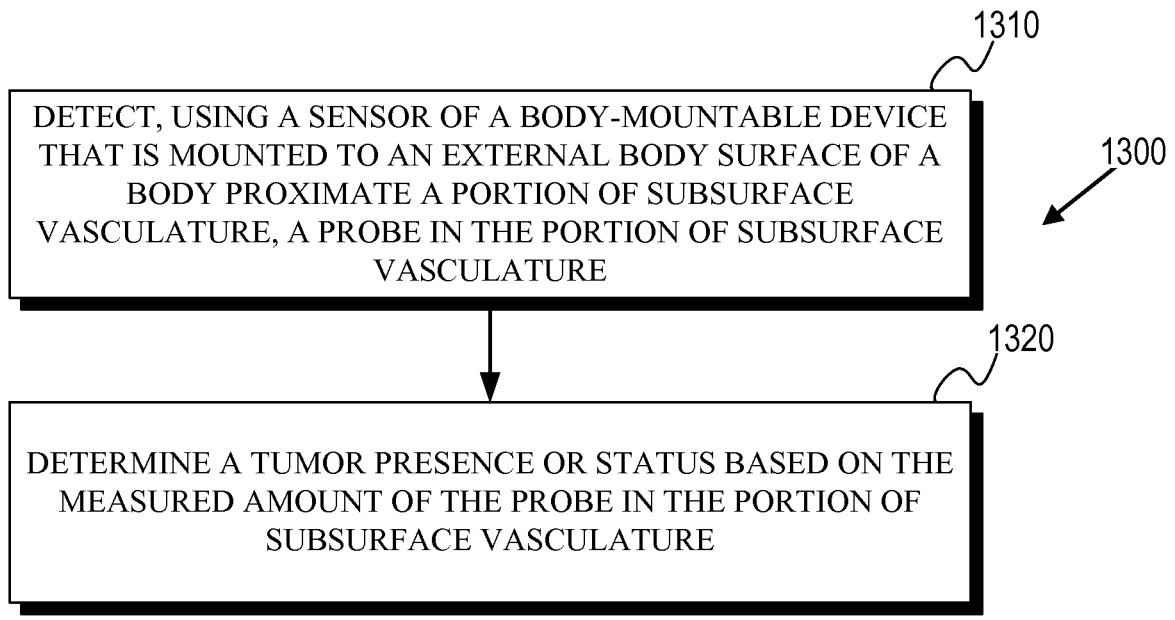
FIG. 13 is a flowchart of an example method.

FIG. 13 is a flowchart of an example method 1300 for determining the presence or status of a tumor in a body by detecting, using a body-mountable device mounted to the body, a probe as described elsewhere herein that is disposed in a portion of subsurface vasculature of the body. The body-mountable device includes a sensor and is mounted to an external body surface of a body (e.g., a wrist surface) proximate a portion of subsurface vasculature (e.g., a portion of vasculature in a wrist). The probe is configured to associate with tumor cells before the tumor cells metastasize and to remain associated with the tumor cells after the tumor cells have metastasized.

The method 1300 includes detecting, using the sensor of the body-mountable device, the probe in the portion of subsurface vasculature (1310). Detecting the probe in the portion of subsurface vasculature includes measuring an amount of the probe in the portion of subsurface vasculature. Detecting the probe (1310) could include detecting the presence of the probe in the portion of subsurface vasculature, detecting a number or concentration of the probe in the portion of subsurface vasculature, detecting a rate or timing at which the probe is present in the portion of subsurface vasculature, or detecting some other measure of the timing or amount of the presence of the probe in the portion of subsurface vasculature.

Detecting, using the sensor of the body-mountable device, the probe in the portion of subsurface vasculature (1310) could include detecting a light, a magnetic field, or some other physical variable that is related to the probe. For example, the sensor could be used to detect an intensity, a spectrum, a color, or some other property of light reflected, refracted, fluorescently absorbed and re-emitted, scattered, or otherwise emitted by the probe (e.g., by a fluorophore, chromophore, Raman dye, fluorescent nanodiamond, or other element of the probe). Additionally or alternatively, the sensor could be used to directly or indirectly detect a magnetic field produced by the probe (e.g., by a nanoparticle of superparamagnetic iron or other magnetic element of the probe). The sensor could be used to detect some other physical variable that is related to the presence of the probe in the portion of subsurface vasculature proximate the sensor.

The method 1300 additionally includes determining a tumor presence or status based on the measured amount of the probe in the portion of subsurface vasculature (1320). In particular, as the probe is configured to associate with tumor cells before the tumor cells metastasize and to remain associated with the tumor cells after the tumor cells have metastasized, the presence of a tumor, a size of a tumor, a type of a tumor (e.g., if the probe is configured to selectively associate with tumor cells of a particular tumor type), a rate or degree of metastasis of a tumor, or some other information about the presence or status of a tumor could be determined based on the measured amount of probe in the portion of subsurface vasculature. Such determinations could additionally or alternatively be based on a rate or frequency at which the probe is detected in the portion of subsurface vasculature and/or a timing of detection of the probe relative to, e.g., introduction of the probe into the body.

Additionally or alternatively, if the probe has a property that is indicative of the probe having interacted with a tumor, the presence of a tumor, a size of a tumor, a degree of perfusion of a tumor, a type of a tumor (e.g., if the property of the probe is indicative of interaction with a particular tumor type), a property of the environment of a tumor (e.g., a pH level in the tumor), a property of the interaction between a tumor and the probe (e.g., a duration of time during which the probe was exposed to a tumor), or some other information about the presence or status of a tumor could be determined by using the sensor to measure such a property of the probe. Additional or alternative methods of determining the presence, or other information, of a tumor in a body based on detected properties of a probe in a portion of subsurface vasculature are anticipated.

The method 1300 could include additional steps or elements. For example, the method 1300 could include exerting an attractive magnetic field (e.g., from a magnetic flux source of the body-mountable device) to collect magnetic nanoparticle-containing probes, e.g., to extract the probes and/or to increase a magnitude of a signal produced by the probe as detected by the sensor of the body-mountable device. The method 1300 could include introducing the probe into the body by injecting the probe using a hypodermic syringe, via a catheter, via an intravenous port, via a transdermal patch or other transdermal delivery means, or via some other means for accessing the vasculature. Additionally or alternatively, the probe could be introduced orally (e.g., in a pill or other ingestible substance) and could be absorbed by the body into the bloodstream. The method 1300 could include additional or alternative steps.

VII. CONCLUSION

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

Where example embodiments involve information related to a person or a device of a person, such embodiments may include privacy controls. Such privacy controls may include, at least, anonymization of device identifiers, transparency and user controls, including functionality that would enable users to modify or delete information relating to the user's use of a product.

Further, in situations wherein embodiments discussed herein collect personal information about users, or make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. A system comprising:
    a probe, wherein the probe comprises at least one of (i) a tumor-binding agent that experiences a conformation change in response to exposure to a tumor environment such that the tumor-binding agent can bind to tumor cells when exposed to the tumor environment or (ii) an interfering element or protective layer that is capable of preventing the probe from binding to tumor cells and that is disabled in response to exposure to a tumor environment such that the probe can bind to tumor cells when exposed to the tumor environment, whereby the probe selectively associates with tumor cells before the tumor cells metastasize, and wherein the probe is configured to be able to remain associated with the tumor cells after the tumor cells have metastasized; and
    a body-mountable device, wherein the body-mountable device comprises:
        a sensor configured to be mounted to an external body surface of a body proximate a portion of subsurface vasculature, wherein the sensor is configured to detect the probe in the portion of subsurface vasculature; and
        a controller operably coupled to the sensor, wherein the controller comprises a computing device programmed to perform controller operations comprising:
            operating the sensor to detect the probe, wherein detecting the probe comprises measuring an amount of the probe in the portion of subsurface vasculature; and
            determining a tumor presence or status based on the measured amount of the probe in the portion of subsurface vasculature.

2. The system of claim 1, wherein determining a tumor presence or status comprises determining that a tumor is present in the body.

3. The system of claim 1, wherein determining a tumor presence or status comprises determining a degree of metastasis of a tumor in the body.

4. The system of claim 1, wherein the body-mountable device comprises a wearable device.

5. The system of claim 1, wherein the probe comprises a fluorophore, wherein measuring an amount of the probe in the portion of subsurface vasculature comprises detecting an amount of fluorescence light emitted from the portion of subsurface vasculature by the fluorophore, wherein the probe comprises a nanoparticle comprised of a protective material, and wherein the fluorophore is disposed within the protective material.

6. The system of claim 1, wherein the probe comprises a magnetic nanoparticle, wherein measuring an amount of the probe in the portion of subsurface vasculature comprises detecting a magnetic field produced by the magnetic nanoparticle.

7. The system of claim 1, wherein the probe comprises an interfering element that is capable of preventing the probe from binding to tumor cells and that is disabled in response to exposure to a tumor environment such that the probe can bind to tumor cells when exposed to the tumor environment, and wherein the interfering element is disabled by a protease that is characteristic of a tumor environment.

8. The system of claim 1, wherein the probe comprises a tumor-binding agent that experiences a conformation change in response to exposure to a tumor environment such that the tumor-binding agent can bind to tumor cells when exposed to the tumor environment, and wherein the tumor-binding agent experiences a conformation change in response to exposure of the probe to a pH that is characteristic of a tumor environment.

9. The system of claim 1, wherein the probe has a property indicative of whether the probe has interacted with a tumor of the body, wherein the property indicative of whether the probe has interacted with a tumor of the body is related to whether the probe has been exposed to a tumor environment corresponding to a particular tumor type, wherein detecting the probe further comprises measuring the property indicative of whether the probe has interacted with a tumor of the body, and wherein determining a tumor presence or status comprises determining that a tumor of the particular tumor type is present in the body.

10. The system of claim 1, wherein the probe comprises a magnetic nanoparticle, and further comprising:
    a magnetic flux source configured to be mounted to the external body surface, wherein the magnetic flux source is configured to exert an attractive magnetic force on the magnetic nanoparticle to collect the probe in the portion of subsurface vasculature proximate the sensor.

11. A method comprising:

introducing a probe into a body, wherein the probe comprises at least one of (i) a tumor-binding agent that experiences a conformation change in response to exposure to a tumor environment such that the tumor-binding agent can bind to tumor cells when exposed to the tumor environment or (ii) an interfering element or protective layer that is capable of preventing the probe from binding to tumor cells and that is disabled in response to exposure to a tumor environment such that the probe can bind to tumor cells when exposed to the tumor environment, whereby the probe selectively associates with tumor cells before the tumor cells metastasize, and wherein the probe is configured to be able to remain associated with the tumor cells after the tumor cells have metastasized; and operating a body-mountable device comprising a sensor mounted to an external body surface of the body proximate a portion of subsurface vasculature, wherein the body-mountable device comprises a sensor configured to detect the probe in the portion of the subsurface vasculature, wherein operating the body-mountable device comprises:

detecting, using the sensor of the body-mountable device, the probe in the portion of subsurface vasculature, wherein detecting the probe comprises measuring an amount of the probe in the portion of subsurface vasculature; and determining a tumor presence or status based on the measured amount of the probe in the portion of subsurface vasculature.

12. The method of claim 11, wherein determining a tumor presence or status comprises determining that a tumor is present in the body.

13. The method of claim 11, wherein determining a tumor presence or status comprises determining a degree of metastasis of a tumor in the body.

14. The method of claim 11, wherein the probe comprises at least one of an X-ray contrast agent or a magnetic resonance contrast agent.

15. The method of claim 11, wherein the probe comprises a fluorophore, wherein measuring an amount of the probe in the portion of subsurface vasculature comprises detecting an amount of fluorescence light emitted from the portion of subsurface vasculature by the fluorophore, wherein the probe comprises a nanoparticle comprised of a protective material, and wherein fluorophore is disposed within the protective material.

16. The method of claim 11, wherein the probe comprises a magnetic nanoparticle, wherein measuring an amount of the probe in the portion of subsurface vasculature comprises detecting a magnetic field produced by the magnetic nanoparticle.

17. The method of claim 11, wherein the probe comprises an interfering element that is capable of preventing the probe from binding to tumor cells and that is disabled in response to exposure to a tumor environment such that the probe can bind to tumor cells when exposed to the tumor environment, and wherein the interfering element is disabled by a protease that is characteristic of a tumor environment.

18. The method device of claim 11, wherein the probe comprises a tumor-binding agent that experiences a conformation change in response to exposure to a tumor environment such that the tumor-binding agent can bind to tumor cells when exposed to the tumor environment, and wherein the tumor-binding agent experiences a conformation change in response to exposure of the probe to a pH that is characteristic of a tumor environment.

19. The method of claim 11, wherein the probe has a property indicative of whether the probe has interacted with a tumor of the body, wherein the property indicative of whether the probe has interacted with a tumor of the body is related to whether the probe has been exposed to a tumor environment corresponding to a particular tumor type, wherein detecting the probe further comprises measuring the property indicative of whether the probe has interacted with a tumor of the body, and wherein determining a tumor presence or status comprises determining that a tumor of the particular tumor type is present in the body.

20. The method of claim 11, wherein the probe comprises a magnetic nanoparticle, wherein the body-mountable device further comprises a magnetic flux source configured to be mounted to the external body surface, and wherein operating the body-mountable device further comprises:

exerting, using the magnetic flux source, an attractive magnetic force on the magnetic nanoparticle to collect the probe in the portion of subsurface vasculature proximate the sensor.

* * * * *